US010302607B2

United States Patent
Walsh et al.

(10) Patent No.: US 10,302,607 B2
(45) Date of Patent: May 28, 2019

(54) METHOD FOR DETAILED AND BULK CLASSIFICATION ANALYSIS OF COMPLEX SAMPLES USING VACUUM ULTRA-VIOLET SPECTROSCOPY AND GAS CHROMATOGRAPHY

(71) Applicant: VUV Analytics, Inc., Cedar Park, TX (US)

(72) Inventors: Phillip Walsh, Austin, TX (US); Dale A. Harrison, Austin, TX (US); Sean H. Jameson, Jr., Lakeway, TX (US)

(73) Assignee: VUV Analytics, Inc., Cedar Park, TX (US)

( * ) Notice: Subject to any disclaimer, the term of this patent is extended or adjusted under 35 U.S.C. 154(b) by 190 days.

(21) Appl. No.: 15/175,175

(22) Filed: Jun. 7, 2016

(65) Prior Publication Data

US 2016/0363569 A1 Dec. 15, 2016

Related U.S. Application Data

(63) Continuation of application No. 62/173,605, filed on Jun. 10, 2015.

(51) Int. Cl.
| | |
|---|---|
| *G01N 31/00* | (2006.01) |
| *G01N 30/86* | (2006.01) |
| *G01N 30/74* | (2006.01) |
| *G01N 33/28* | (2006.01) |

(52) U.S. Cl.
CPC ......... *G01N 30/8693* (2013.01); *G01N 30/74* (2013.01); *G01N 30/8617* (2013.01);
(Continued)

(58) Field of Classification Search
CPC ............... G01N 30/8693; G01N 30/74; G01N 30/8617; G01N 30/8644
(Continued)

(56) References Cited

U.S. PATENT DOCUMENTS

| | | |
|---|---|---|
| 4,807,148 A | 2/1989 | Lacey |
| 5,212,096 A | 5/1993 | Kolhouse et al. |

(Continued)

FOREIGN PATENT DOCUMENTS

WO 2012/143901 10/2012

OTHER PUBLICATIONS

International Preliminary Report, PCT/US2016/036153; dated Dec. 21, 2017,10 pgs.
(Continued)

*Primary Examiner* — Toan M Le
*Assistant Examiner* — Xiuqin Sun
(74) *Attorney, Agent, or Firm* — Egan Peterman Enders Huston

(57) ABSTRACT

Analysis of chemically samples using gas chromatography (GC) separation with vacuum ultra-violet spectroscopy detection is described. One technique focuses on assigning a specific analysis methodology to each constituent in a sample. Constituents can elute from the GC by themselves or with other constituents, in which case a deconvolution is done using VUV spectroscopic data. In an exemplary embodiment, each constituent may be specifically included in an analysis method during a setup procedure, after which the same series of analyses are done on subsequent sample runs. The second approach essentially integrates an entire chromatogram by first reducing it into a series of analysis windows, or time slices, that are analyzed automatically. The analysis at each time slice determines the molecular constituents that are present as well as their contributions to the total response. Either approach can be used to quantify specific analytes or to do bulk classification.

29 Claims, 21 Drawing Sheets

(52) U.S. Cl.
CPC ..... *G01N 30/8644* (2013.01); *G01N 30/8686* (2013.01); *G01N 33/2835* (2013.01)

(58) Field of Classification Search
USPC .......................................................... 702/27
See application file for complete search history.

(56) References Cited

U.S. PATENT DOCUMENTS

| | | | |
|---|---|---|---|
| 5,686,655 | A | 11/1997 | Itoi |
| 9,116,158 | B2 | 8/2015 | Harrison et al. |
| 2005/0232929 | A1 | 10/2005 | Kadkhodayan et al. |
| 2011/0246092 | A1* | 10/2011 | Wright ............... G01N 30/8624 702/32 |
| 2012/0135094 | A1* | 5/2012 | Simon .................... A61K 36/53 424/745 |
| 2013/0224870 | A1* | 8/2013 | Vigh ................ G01N 33/54306 436/86 |
| 2014/0192343 | A1* | 7/2014 | Harrison ................... G01J 3/02 356/51 |
| 2015/0107331 | A1* | 4/2015 | Wang ..................... G01N 30/72 73/23.37 |

OTHER PUBLICATIONS

International Search Report, PCT/US2016/036153; dated Sep. 2, 2016, 10 pgs.

Schug et al., "Vacuum Ultraviolet Detector for Gas Chromatography," May 16, 2014, 7 pp.

Bai at al., "Permanent gas analysis using gas chromatography with vacuum ultraviolet detection," Feb. 3, 2015, 7 pp.

Fan et al., "Gas chromatography—vacuum ultraviolet spectroscopy for multiclass pesticide identification," Feb. 11, 2015, 8 pp.

Analytical Controls, "Comparison of ASTM D 6730 (DHA) and ASTM D 6839 (Piona/Reformulyzer)" 2006 , 19 pp.

Van den Heuval et al., "Take Advantage of Better PIONA Analysis," Apr. 2012, 2 pp.

ASTM International, D6730 "Standard Test Method for Determination of Individual Components in Spark Ignition Engine Fuels by 100-Metre Capillary (with Precolumn) High-Resolution Gas Chromatography," Apr. 2007, 55 pp.

ASTM International, D6839 "Standard Test Method for Hydrocarbon Types, Oxygenated Compounds and Benzene in Spark Ignition Engine Fuels by Gas Chromatography," 2007, 9 pp.

Zimmermann et al., "Comprehensive two-dimensional gas chromatography coupled to vacuum ultraviolet spectroscopy," May 22, 2014, 13 pp.

Global Analyser Solutions, Application Note 213WA0907C SI-PIONA analyser Single column GC-MS method, 2014 or earlier, 4 pp.

Extended European Search Report, 16808108.1; PCT/US2016/036153; dated Feb. 11, 2019, 9 pgs.

* cited by examiner

METHOD FOR DETAILED AND BULK CLASSIFICATION ANALYSIS OF COMPLEX SAMPLES USING VACUUM ULTRA-VIOLET SPECTROSCOPY AND GAS CHROMATOGRAPHY

This application claims priority to Provisional Patent Application No. 62/173,605 filed Jun. 10, 2015, the disclosure of which is expressly incorporated herein by reference.

BACKGROUND OF THE INVENTION

The present disclosure relates to the field of absorption spectroscopy. More specifically, it provides a means for analysis of chemically complex samples using gas chromatography (GC) separation with vacuum ultra-violet (VUV) spectroscopy detection.

There are a wide variety of complex chemical samples for which analysis may be desired. A particular type of known sample analysis is the analysis of hydrocarbon content in petroleum-based fuels such as unleaded gasoline, jet fuel, and diesel fuel. However other complex liquid and gas samples are known to be subject to analysis, including but not limited to food products, fragrances, etc. For the purposes of this specification, the term "complex" refers to samples containing many constituents, often hundreds or more constituents, the constituents generally being distinct molecular species that can largely be separated by a chromatographic separation process.

One example of a "complex" sample for which analysis is often desired is petroleum-based liquid fuels. Petroleum fuels can consist of several hundred to several thousand distinct components. Most of the molecular components of petroleum products fall into one of a handful of distinct categories. For example, saturated hydrocarbons are carbon and hydrogen containing compounds where all bonds between carbon atoms are single bonds. Saturated hydrocarbons can be thought of as being saturated with hydrogen atoms, as they have the largest number of hydrogen atoms possible given the number of carbon atoms present and their conformational structure. Replacing one or more of the single carbon-carbon bonds with double bonds reduces the degree of saturation. Saturated hydrocarbons are often further classified into linear chain paraffins, branched chain isoparaffins, and cyclic naphthenes. Unsaturated hydrocarbons where one or more double carbon-carbon bonds exist are known as olefins, diolefins, or polyolefins. Aromatic compounds are ring structures that contain some degree of aromaticity. The simplest is benzene, consisting of a six-membered carbon ring, with six of its electrons being completely delocalized. Benzene is sometimes also represented as a ring structure with three alternating double carbon-carbon bonds. Various other aromatic compounds consist of a benzene base with some of the hydrogen atoms replaced by various other functional groups. For example, toluene is a benzene derivative with a methyl group replacing one of the hydrogen atoms. Aromatic compounds that contain a single aromatic ring are often known as monocyclic aromatic hydrocarbons, or simply mono-aromatic compounds. Multiple ring aromatic compounds also exist, and are often known as polycyclic aromatic hydrocarbons (PAHs). The simplest PAH with fused aromatic rings is naphthalene. The simplest PAH with two separated aromatic rings is biphenyl. As in the case of mono-aromatic compounds, a large variety of compounds are possible having one of these bases along with various functional groups replacing the terminating hydrogen atoms. Molecules that have PAH cores with substituents in place of some of the hydrogen atoms are not technically PAHs, but they are still commonly referred to as such, and this practice will also be used in the current specification. For the purposes of this specification, the term "poly-aromatic" is also used as a generic term for molecules having multiple (two or more) aromatic rings.

Some specific molecular components are of particular importance in fuel analysis, such as iso-octane or benzene. Individual oxygenates such as ethanol can also be important. However, a variety of properties of petroleum-based fuels depend mainly on the relative amounts of bulk classes of compounds. For example, measurement of bulk concentration of the various hydrocarbon classes is important for fuel production control. The total amount of aromatics is often regulated due to environmental concerns. Olefin content is also highly regulated in some markets, especially in Europe.

One type of bulk classification of gasoline-range fuels is characterization of relative mass or weight content of each of the five hydrocarbon groups of paraffins, isoparaffins, olefins, naphthenes, and aromatics (for the purposes of this specification, the terms mass percent and weight percent will be used interchangeably). This type of analysis is often known by its acronym PIONA. Combinations of hydrocarbon classes may be used to obtain other types of bulk classifications. For example, the three classes of saturated hydrocarbons included in a PIONA analysis are sometimes combined to quantify the total amount of saturated hydrocarbons in a sample. Such analysis may further determine bulk mono-aromatic and bulk poly-aromatic content of a fuel sample. Classification of hydrocarbon classes can be accompanied by characterization of specific molecular species in a sample, such as quantifying individual oxygenates or members of the BTEX (benzene, toluene, ethylbenzene, xylenes) aromatics complex.

Gas chromatography is an analytical method for separating complex mixtures into their constituent components, which are then quantified and/or identified using a variety of detectors. A typical mode of operation for a GC experiment is to vaporize a small amount (typically 0.1-1 µL) of liquid sample and forcing it via pressurized carrier gas onto the head of an analytical column. The carrier gas is also known as the mobile phase, and is usually an inert gas such as nitrogen or helium. In a common type of GC, known as capillary GC, the analytical column is a long, 15-100 m fused silica capillary whose inner walls are coated with a film coating known as a stationary phase. A pressure differential is maintained between head and detector ends of the column, causing the carrier gas to continuously flow through the column. The analytical column is contained in an oven. The starting temperature of the oven is usually room temperature or lower, and a significant portion of the vaporized sample will re-condense at the head of the analytical column. The oven temperature is then gradually increased, liberating condensed species into the mobile phase in a manner consistent with the species' boiling points. The stationary phase interacts with the various molecular constituents traversing the column, retaining them differently depending on the species' chemical makeup. Thus the separation process consists of a gross separation depending on constituent boiling point combined with a stationary phase separation driven by the chemistry of interaction between constituent molecules and stationary phase molecules. The result is that the individual constituents making up the original sample elute from the column at different times. For a thorough separation process, each molecular constituent elutes at a unique elution time. This is not always possible, however, and it is possible that multiple distinct species will coelute at a given elution time. The term "analyte" is used often throughout this disclosure to describe a molecular species that elutes from the analytical column during a GC experiment.

One of a variety of detectors is placed at the end of the analytical column, generating a signal when analyte molecules exit the column. The detector response signal as a function of time is known as a chromatogram. The distribution for most compounds is driven by random interaction with the column phase as they traverse the column and tends toward Gaussian. The chromatogram of a well-separated mixture consists of a series of approximately Gaussian shaped "peaks", each representing the elution of one of the analyte constituents.

For the simplest type of chromatogram consisting of a plot of response versus time, the elution time is used to identify the compounds. An analyte's elution time is also known as its retention time, and is specific to a given GC method and analytical column. The size of the response, either the height or area of the peaks, is used to quantify the amount of the constituents. In most cases, a relative measurement is done, and the relative amounts of various constituents and solvent are used to determine constituent concentration in the original liquid sample.

The most common gas chromatographic detector for hydrocarbon analysis is the flame ionization detector. Flame ionization detection (FID) shows good sensitivity and linearity to carbon-containing compounds. In addition, FID is generally cheap and robust. The main disadvantages of FID are insensitivity to some compounds of interest, such as carbon dioxide and water, but especially the inherently one-dimensional response. The FID has no ability to distinguish between different compounds, and in particular has no ability to deal with coelution, i.e., when multiple compounds elute simultaneously from the analytical column. This means that complete separation has to be achieved in order to quantify individual compounds in a substance. GC-FID analyte identification is only possible by using the elution order of compounds from a sample. For a substance containing many individual constituents, like petroleum-based fuels, very accurate knowledge of elution order is required, and this elution order must be strictly maintained from run to run. A method describing a GC-FID methodology for analysis of refined gasoline samples is given in the American Society for Testing and Materials (ASTM) method D6730. The type of analysis done in this method is often referred to as detailed hydrocarbon analysis (DHA), and focuses on identifying and quantifying as many specific compounds as possible in a gasoline mixture. The requirement for complete separation results in an extremely long run time of up to three hours ("fast" DHA methods claim to accomplish this in about 1½ hours). The requirement for strictly establishing and maintaining elution order results in a very complicated setup procedure. Since analytical columns degrade with use, the setup procedure has to be done periodically when the analytical columns are replaced.

Coelution can be tolerated if bulk classification is desired, but even in this case complete separation by analyte class is still necessary. In the case of fuel analysis, this results in very complicated separations involving multiple columns, traps, and switching valves. An example of such an apparatus, also known as a reformulyzer, is described in ASTM D6839. The reformulyzer is difficult to set up and maintain, and run times tend to be long, typically consisting of an hour or more.

Other GC detectors add a level of identification capability independent of the elution time. Mass spectrometry fragments eluting analytes into characteristic mass spectra, in the form of a response versus mass-to-charge ratio. Mass spectrometry is a mature technology and large libraries exist enabling identification for a large number of unknown compounds in a sample. As a GC detection technique, mass spectrometry has several disadvantages. It is inherently destructive. It is insensitive to several types of compounds and only very elaborate and expensive variations can distinguish between structural isomers or stereoisomers of the same compound. Also, mass spectra can be very difficult to interpret and lack intuitive class-based features that result in easy molecular class identification.

Infra-red (IR) spectra can be used to distinguish compounds from each other, but IR wavelengths are completely insensitive to ground state to excited state electronic transitions, tending to be sensitive to much lower cross-section vibrational transitions. As such, IR absorbance is much less sensitive to a given amount of molecule than VUV absorbance spectra. In addition, quantification using IR spectroscopy is challenging due to difficulties associated with maintaining the high resolution requirements, both in terms of tool matching and variation in individual instruments over time.

In spite of being mature, prolific technologies, neither mass spectrometry nor IR spectrometry has become a serious contender for bulk classification analysis of complex samples in general. In the particular case of complex fuel mixtures, ASTM methods like D6730 and D6839 remain the dominant methods of analysis.

It would be desirable to have an improved method for analyzing complex samples.

SUMMARY OF THE INVENTION

The disclosure herein provides a method for analysis of chemically complex samples using gas chromatography (GC) separation with vacuum ultra-violet (VUV) spectroscopy detection. A particular application of the method is the analysis of hydrocarbon content in petroleum-based fuels such as unleaded gasoline, jet fuel, and diesel fuel though it is noted that examples of complex samples exist in many other fields including but not limited to food products, fragrances, etc. Examples using liquid petroleum fuel samples, in particular refined unleaded gasoline, are provided within the disclosure. However, the methodology can be applied to practically any complex liquid or gas sample. Furthermore, though described herein with regard to complex samples, it would clearly be recognized that the methodology that works for "complex" samples can be applied as well to the analysis of chemically "simple" samples that consist of just a few constituents.

The disclosure provided herein distinguishes between two approaches to complex sample analysis. One approach is referred to as the "detailed" approach, and focuses on assigning a specific analysis methodology to each constituent in a sample. Constituents can elute from the GC by themselves or can coelute with other constituents, in which case a deconvolution is done using VUV spectroscopic data. In one exemplary embodiment of the first approach, each constituent may be specifically included in an analysis method during a setup procedure, after which the same series of analyses are done on subsequent sample runs.

The second approach essentially integrates an entire chromatogram by first reducing it into a series of analysis windows, or time slices, that are analyzed automatically. The analysis at each time slice determines the molecular constituents that are present as well as their contributions to the total response. Either approach can be used to quantify specific analytes or to do bulk classification. However, this second approach lends itself particularly well to bulk classification analysis of complex samples, and so is referred to herein as the "classification" approach. An aspect of this approach is that it is not necessary to explicitly determine the shapes of response peaks from coeluting analytes in order to determine their individual contributions to the total response.

A primary aspect of the current specification is the use of VUV spectroscopy detection in conjunction with GC separation. Advantages of VUV spectroscopy as a gas chromatography detector over existing detection techniques are numerous, as is described at various points in the specification. In one embodiment, a 125-240 nm VUV absorbance spectrum is measured during each scan, with a scan rate of anywhere from 2 to 100 Hz. When a VUV spectroscopy detector is used at the end of a GC separation, the GC-VUV dataset is inherently three dimensional, consisting of response versus wavelength versus time. In one embodiment, the response is absorbance, although other types of response, such as transmittance can also be obtained from spectroscopic measurements.

In one embodiment, a method of analyzing a multi-constituent chemical sample is provided. The method may comprise providing a chromatograph, the chromatograph configured to elute from the chemical sample a plurality of analytes to be analyzed and providing a spectrometer to analyze the plurality of analytes, the spectrometer capable of measuring multiple wavelengths of light, and when coupled with the chromatograph providing wavelength dependent and time dependent chromatographic data. The method may further include dividing the chromatographic data into a plurality of time segments; determining contributions of one or more of the analytes that elute in a particular time segment, the determining contributions accomplished, at least in part, by applying, for at least some of said time segments, a deconvolution model to the chromatographic data; and combining, for one or more time segments, results from applying the deconvolution model to determine the contribution of individual or groups of analytes of the multi-constituent chemical sample. The deconvolution model may comprise a combination of reference responses for each of the analytes analyzed.

In another embodiment of the method, the determining step may comprise generating a total chromatographic response for the particular time segment and using the total chromatographic response and the deconvolution model in combination with a tiered search to predict the identities of analytes eluting during the particular time segment, wherein the deconvolution model comprises a combination of reference responses for analytes considered in the tiered search. In this other embodiment, use of the deconvolution model results in a determination of contributions of each of the reference responses to the total chromatographic response for the particular time segment.

In yet another embodiment, a chemical analysis system is provided. The chemical analysis system may comprise a gas chromatograph, the gas chromatograph configured to eluate from a chemical sample a plurality of analytes to be analyzed; a spectrometer to analyze the plurality of analytes, the spectrometer capable of measuring multiple wavelengths of light; and a computer coupled to the spectrometer, data from spectrometer provided to the computer. The computer may be configured to represent data from the spectrometer as wavelength dependent and time dependent chromatographic data, the chromatographic data divided into a plurality of time segments; determine contributions of one or more of the analytes that elute in a particular time segment, the determining contributions accomplished, at least in part, by applying, for at least some of said time segments, a deconvolution model to the chromatographic data; and combine, for one or more time segments, results from applying the deconvolution model to determine the contribution of individual or groups of analytes of the chemical sample. In this embodiment, the deconvolution model comprises a combination of reference responses for each of the analytes analyzed.

In another embodiment of the chemical analysis system, the computer may determine contributions of one or more of the analytes that elute in a particular time segment by a technique that comprises: generating a total chromatographic response for the particular time segment; and using the total chromatographic response and the deconvolution model in combination with a tiered search to predict the identities of analytes eluting during the particular time segment, wherein the deconvolution model comprises a combination of reference responses for analytes considered in the tiered search. In this embodiment, use of the deconvolution model results in a determination of contributions of each of the reference responses to the total chromatographic response for the particular time segment.

In yet another embodiment, a method of analyzing a multi-constituent chemical sample is provided. The method may comprise: providing a gas chromatograph, the gas chromatograph configured to eluate from the chemical sample a plurality of analytes to be analyzed; providing a spectrometer having a two-dimensional detector to analyze the plurality of analytes; and representing data from the spectrometer analysis as wavelength dependent and time dependent chromatographic data, the chromatographic data divided into a plurality of time segments. For each time segment, the method also includes summing chromatographic data for multiple time points in the time segment; generating a total chromatographic response for the time segment using the summed chromatographic data; using the total chromatographic response and a deconvolution model in combination with a tiered search to automatically predict identities of analytes eluting during the time segment; and determining a contribution of each of the referenced responses to the total chromatographic response for the time segment through using deconvolution model. The method further comprises combining results from the determining step of each time segment to provide a total contribution of each analyte predicted to be present in the multi-constituent chemical sample.

BRIEF DESCRIPTION OF THE DRAWINGS

A more complete understanding of the present invention and advantages thereof may be acquired by referring to the following description taken in conjunction with the accompanying drawings, in which like reference numbers indicate like features. It is to be noted, however, that the accompanying drawings illustrate only exemplary embodiments of the disclosed concept and are therefore not to be considered limiting of its scope, for the disclosed concept may admit to other equally effective embodiments.

DESCRIPTION OF THE PREFERRED EMBODIMENTS

Figure 1:
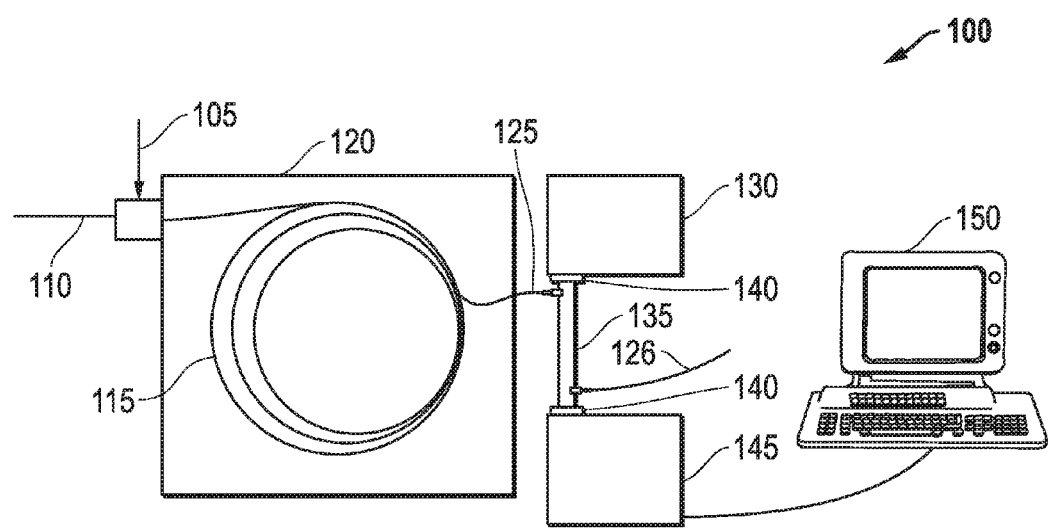
FIG. 1 illustrates an exemplary gas chromatograph vacuum ultra-violet spectroscopy system.

One embodiment of the system for performing the techniques described herein is illustrated in FIG. 1. As shown in FIG. 1, an analysis system 100 is provided that includes a gas chromatograph (GC) having the capability to vaporize liquid samples and move the sample through a GC analytical column. A carrier gas inlet 110 is provided along with a sample injector inlet 105. The carrier gas and sample are provided to a GC column 115. The GC may be equipped with an oven 120 capable of programmed temperature control. The GC may be equipped with a programmable split flow control, and is further capable of operating in either constant inlet pressure or constant flow mode. A VUV spectroscopy detector is connected to the end 125 of the analytical column 115 via a heated transfer tube (transfer tube not explicitly shown in FIG. 1). The VUV spectroscopy detector may include a source module 130 providing a VUV light source, a gas flow cell 135, a spectrometer detector module 145, windows 140 coupling the gas flow cell 135 to the source module 130 and spectrometer detector module 145, and a computing unit 150 electrically coupled to the spectrometer detector module 145. The gas flow cell 135 receives the gas flow from the end 125 of the analytical column 115 and has a gas outlet 126. A computing unit 150 controls the data acquisition of the detector, maintains detector environment control, and stores the output data such as absorbance scans and response chromatograms. Further data processing may be carried out by the computing unit, including either post or real-time processing of scan data to generate qualitative and quantitative information about the injected sample. The computing unit may also be coupled to other elements of the system and store parameters necessary for the operation of the GC, thereby controlling the entire system. Alternately, the GC control electronics may have overall control of the experiment, which starts on sample injection, and the detector is triggered to start data collection when the GC begins its run.

The GC effluent traverses the detector flow cell, which is separated from source and detector modules by VUV transparent windows 140. Typical GC carrier gases are transparent, or at least nearly so, and the flow of carrier gas from the GC is usually sufficient to maintain an oxygen and moisture free environment in the flow cell suitable for propagation of VUV light. The source and detector modules are separately purged with a VUV transparent purge gas such as nitrogen, helium, hydrogen, or argon (not shown). An optional makeup gas, usually consisting of the same gas as the source and detector purge gas, may enter the flow cell near where the GC effluent enters (not shown). When no absorbing species are eluting from the analytical column, the entire light path is substantially free of moisture and oxygen, which would otherwise prevent propagation of VUV light under standard ambient conditions. An exemplary embodiment of a system 100 is further described in U.S. Pat. No. 9,116,158, entitled VACUUM ULTRAVIOLET ABSORPTION SPECTROSCOPY SYSTEM AND METHOD, by Harrison et al., the disclosure of which is expressly incorporated by reference. It will be recognized that other systems may be utilized however to achieve the techniques described herein.

A reference scan is collected under these conditions, after which the absorbance of the flow cell is continuously measured. The scan rate can be as high as 100's or even 1000's of cycles/second, but scan rates of 5-10 scans/second are typical. In one embodiment, the full range absorbance is analyzed to identify and quantify molecular constituents. However, producing two-dimensional chromatographic data from the three dimensional dataset is also useful. To do this, the absorbance spectra are integrated over specific wavelength regions, referred to herein as integration filters. For example, a full range response might be generated consisting of the average absorbance over the entire measured spectrum. This is done for each scan, and the resulting chromatogram is a plot of average absorbance versus time. A second integration might consist of average absorbance over the 170-200 nm wavelength region, which is particularly sensitive to mono-aromatic compounds. Any number of integration filters are possible and can be plotted simultaneously. Thus, a single chromatographic run can yield any number of separate two-dimensional chromatograms. For this purpose, the term "integration" refers to any operation performed on the wavelength-dependent absorbance spectrum intended to generate a single scalar response value. The operation can consist of averaging, summing, true integration (with units of absorbance multiplied by wavelength), etc. An integration filter can also invoke arithmetic, geometric, or logical operations on multiple wavelength regions. For example, an integration filter can consist of the average absorbance of the 170-200 nm region subtracted from the average absorbance of the 125-240 nm region. This filter produces a negative response to mono-aromatic compounds.

Taking fuller advantage of the three-dimensional nature of GC-VUV data, the response versus wavelength information provides the ability to identify molecular components without knowledge of elution order. One way to identify molecular species by their absorbance spectra is to compare a measured absorbance to reference absorbance spectra contained in a reference library, referred to herein as the "VUV reference library". As is described in more detail below, the shape of a molecule's absorbance spectrum depends on the molecule's electronic structure, and the overall scale of the absorbance depends on the amount of the molecule present when the absorbance is measured. Therefore, the shape of an analyte's absorbance spectrum can be used to identify the analyte when its absorbance is measured again at a later time. The VUV reference library is a collection of absorbance spectra for various compounds measured during GC-VUV experiments of various prepared standards contrived to present each analyte to the detector without the influence of other analytes.

The response versus wavelength also provides the ability to deconvolve chromatographic events involving coelution into their constituent components. In other words, VUV absorbance spectra provide a means of separation independent of elution time. Depending on the type of molecules involved in a coelution, it may be completely resolved by VUV spectra alone. For other coelution problems, approximate elution time may still be helpful in eliminating a large subset of candidate molecules from the general reference library. The remaining set can still be relatively large, so the control of elution order does not need to be as exact as in the case of GC-FID. For one exemplary embodiment of GC-VUV, the combination of approximate elution information and spectral information contributes to a powerful solution to liquid fuel analysis.

VUV absorbance is sensitive primarily to molecular electronic structure. VUV absorbance spectra often exhibit vibrational and rotational structure superimposed on the electronic structure, making for rich, feature-filled spectra that are unique for a given molecule. VUV absorbance spectra of gasses often provide powerful "fingerprinting" capability for distinguishing molecular species.

VUV absorbance spectra also benefit from the intuitive property that molecules having similar molecular structures exhibit similarities in their absorbance characteristics. This aspect of VUV absorbance lends itself particularly well to complex sample analysis where bulk classification is of primary concern. Instead of specifically characterizing every molecular constituent in a mixture, broader classes of molecules can be identified and associated with collections of "basis" reference spectra, all belonging to the same class.

Figure 2A:
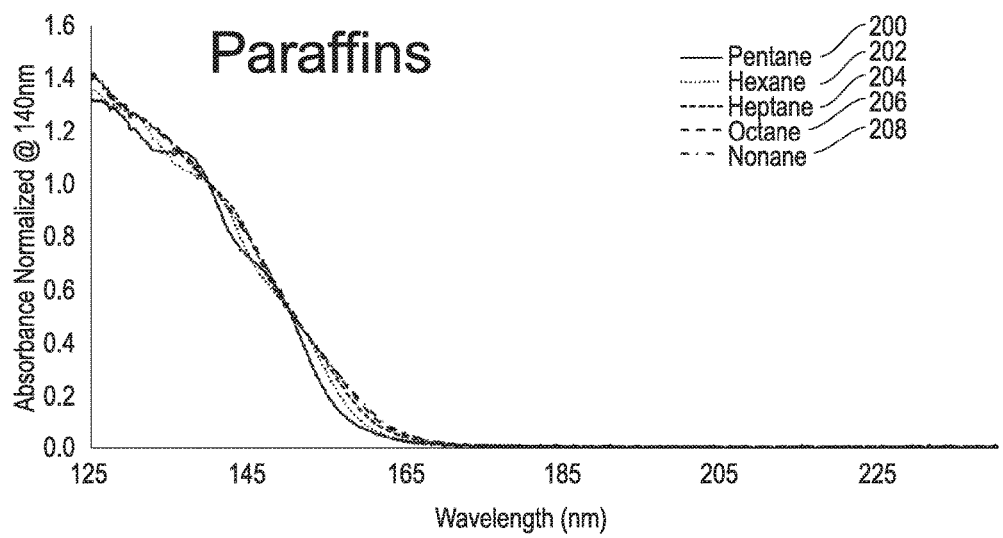
FIGS. 2a-2f illustrate comparisons of 125-240 nm absorbance spectra for various groupings of hydrocarbons.
Figure 2B:
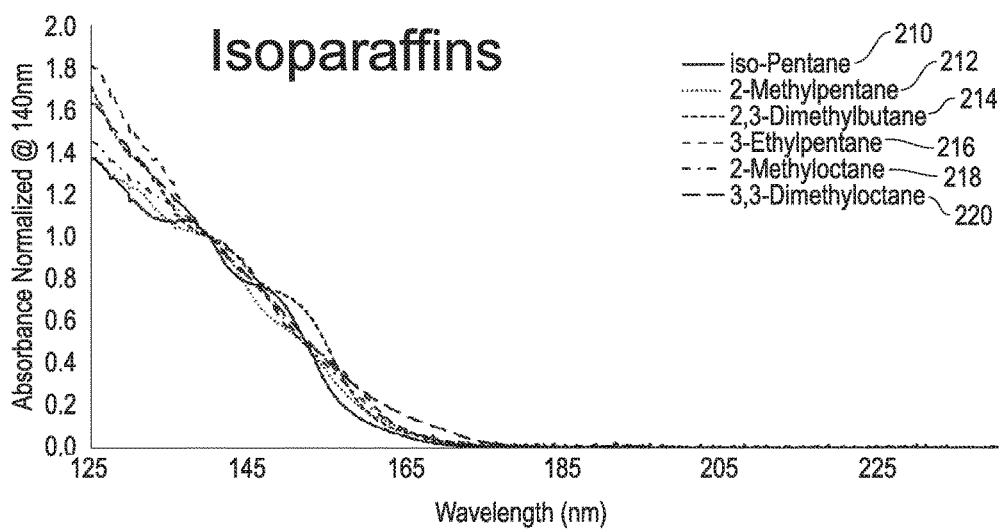
Figure 2C:
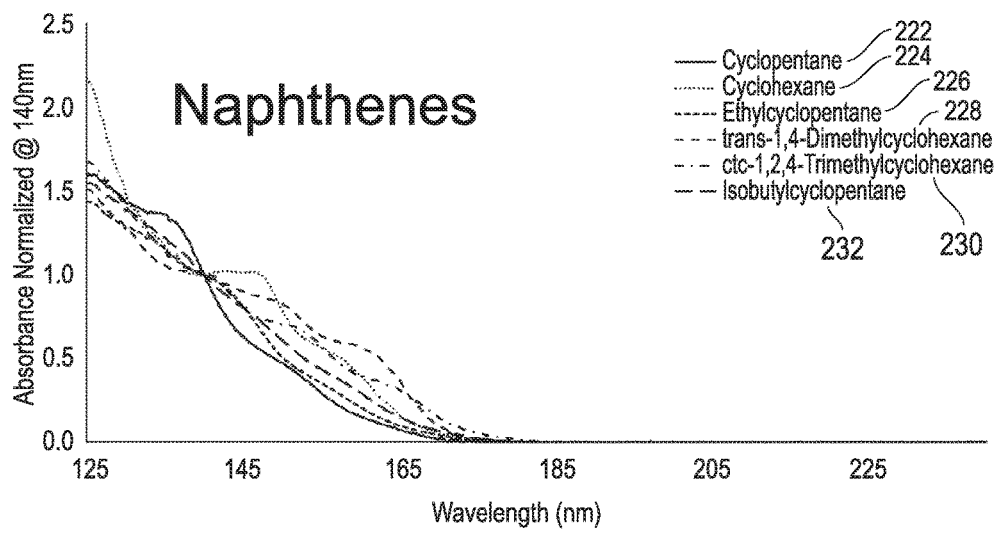
Figure 2D:
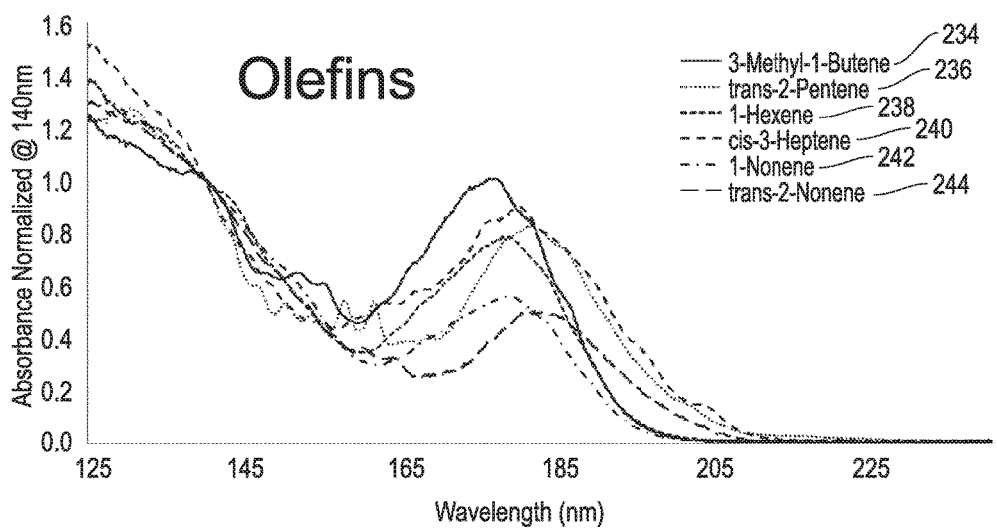
Figures 2E, 2F:
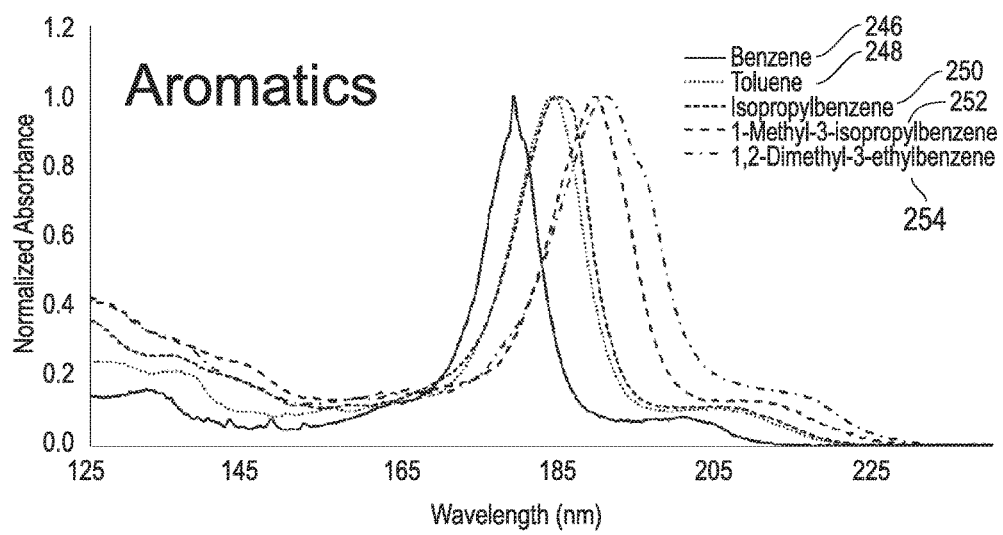

It is important to note that being sensitive to electronic structure, VUV absorbance spectra are sensitive not only to molecular structure and shape but also to the types of chemical bonds present. In particular, hydrocarbon absorption spectra are extremely sensitive to the degree of saturation of the measured molecules. FIGS. 2a-2f shows comparisons of 125-240 nm absorbance spectra for several groupings of hydrocarbons. The figures graph the absorbance normalized at 140 nm (FIGS. 2a-2d) or absorbance normalized by the absorbance maxima (FIGS. 2e and 2f) versus wavelength. FIGS. 2a-2c show several paraffins, isoparaffins, and naphthenes, respectively, all saturated hydrocarbon compounds. More particularly, FIG. 2a shows paraffin graphs for pentane 200, hexane 202, heptane 204, octane 206 and nonane 208. FIG. 2b shows isoparaffin graphs for iso-pentane 210, 2-methylpentane 212, 2,3-dimethylbutane 214, 3-ethylpentane 216, 2-methyloctane 218 and 3,3-dimethyloctane 220. FIG. 2c shows naphthene graphs for cyclopentane 222, cyclohexane 224, ethylcyclopentane 226, trans-1,4-dimethylcyclohexane 228, ctc-1,2,4-trimethylcyclohexane 230, and isobutylcyclopentane 232. FIG. 2d shows olefin graphs for 3-methyl-1-butene 234, trans-2-pentene 236, 1-hexene 238, cis-3-heptene 240, 1-nonene 242, and trans-2-nonene 244. FIG. 2e shows aromatic graphs for benzene 246, toluene 248, isopropylbenzene 250, 1-methyl-3-isopropylbenzene 252, and 1,2-dimethyl-3-isopropylbenzene 254. The saturated hydrocarbon groupings are somewhat distinct as are spectra from compounds within each group. But comparing FIGS. 2a-2c for saturated hydrocarbons to FIG. 2d for olefins (one double carbon-carbon bond) and FIG. 2e for aromatics (which can be thought of as having three alternating double bonds) it is apparent that VUV absorbance is particularly sensitive to the presence and number of double bonds in a molecule. Even more remarkable is that some molecules in very different spectral classes have very similar molecular characteristics. For example, 1-hexene and cyclohexane have identical molecular weight and chemical formulas, and are basically indistinguishable to mass spectrometry. Yet the VUV absorbance spectra for these two compounds are very different as shown in FIG. 2f which compares the 1-hexene graph 260 to the cyclohexane graph 262.

The spectra presented in FIGS. 2a-2f show that one of the primary spectral groupings relevant to fuel analysis is classification by saturated hydrocarbons, olefinic content, and aromatic content. A secondary classification can occur within the saturated hydrocarbon groups of paraffins, isoparaffins, and naphthenes, but this grouping is structural instead of by degree of saturation.

Figure 3A:
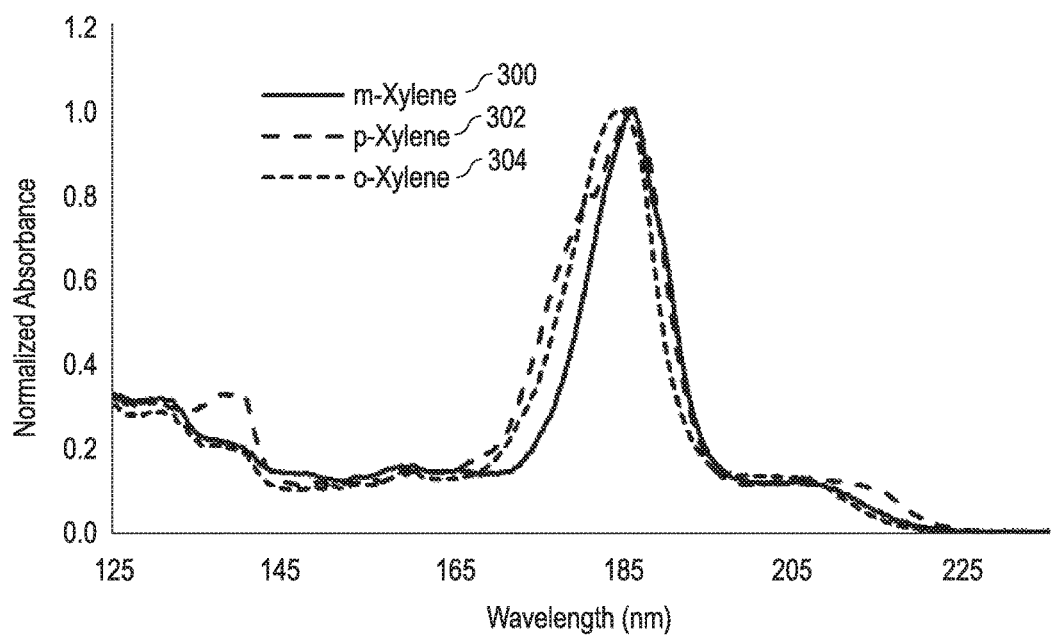
FIGS. 3a-3b illustrates vacuum ultra-violet absorbance spectra of various isomers.
Figure 3B:
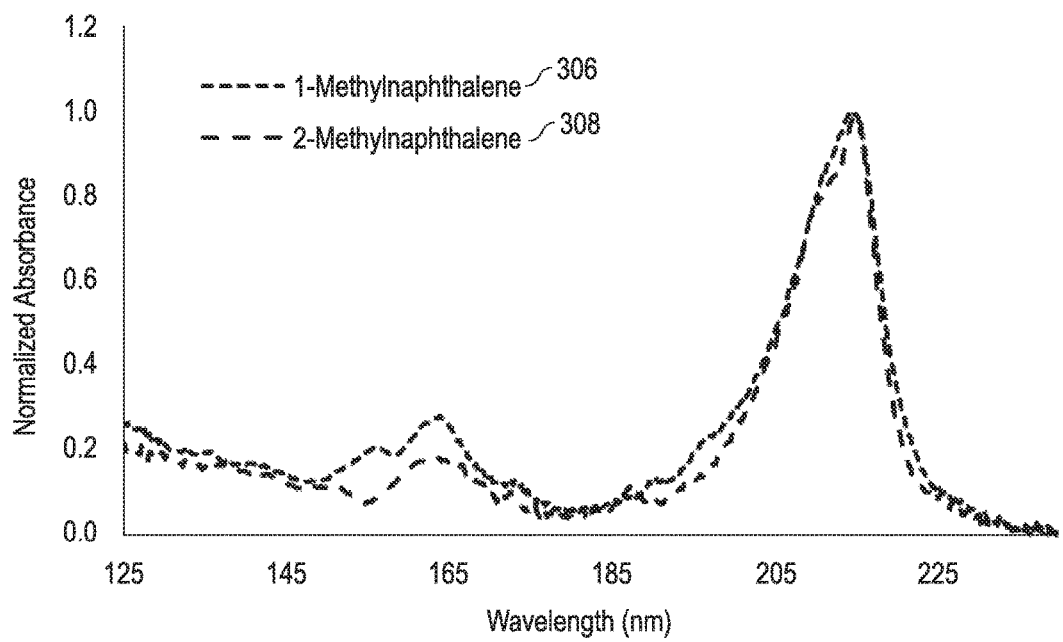

Other important examples of the way underlying molecular structure can affect VUV absorbance spectra can be seen when comparing VUV absorbance of structural isomers. FIGS. 3a and 3b graph normalized absorbance versus wavelength. FIG. 3a compares VUV spectra of meta-xylene 300, para-xylene 302, and ortho-xylene 304 (also known as m-, p-, and o-xylene). These compounds have the same basic structure, consisting of a benzene ring base with two methyl groups attached to two of the carbon atoms. The methyl groups are attached to two different carbon atoms in each isomer, but otherwise the three xylene isomers have identical molecular weight and chemical formula. The mass spectra for each are consequently identical. On the other hand, due to the effect of the molecular structure on the electronic structure, their VUV absorbance spectra are different. This example is particularly important for gasoline analysis since m- and p-xylene coelute under standard GC separation conditions. FIG. 3b shows a similar illustration, but for 1-methylnaphthalene 306 and 2-methylnaphthalene 308. These two isomers of methylnaphthalene are also impossible to distinguish using standard mass spectrometry.

The absorbance A for a given amount, N, of a single type of compound in the flow cell is given by $$A = \frac{1}{\ln(10)} \frac{d}{V} \sigma N \qquad \text{eq. 1}$$

where N is the number of molecules, $\sigma$ is the absorption cross section in $cm^2$/molecule, d is the flow cell length in cm, and V is the flow cell volume in $cm^3$ (note that $d/V=1/X$, where X is the cross sectional area of the flow cell). Obviously, the use of cm for units of length is arbitrary and is chosen here for convenience. $\sigma$ is a property of the molecular species, and in general is different for different molecules. In addition, $\sigma$ is highly wavelength-dependent, so the absorbance in eq. 1 is inherently wavelength dependent. The wavelength dependence of the absorption cross section leads to the unique spectral shapes of different molecular absorbance spectra. V and d are fixed for a given cell geometry. For a given molecule, differences in the amount, N, change the overall magnitude of the absorbance, but not the shape of the absorbance spectrum. Therefore, as a molecular constituent elutes from the GC column, the absorbance spectrum will rise from the baseline floor to some maximum value, and then decline back into the baseline again as the analyte exits the other end of the flow cell. If only a single molecular species is involved, the shape of the absorbance spectrum will not change at any instant of the elution event, only the magnitude will change.

If multiple types of molecules are in the flow cell simultaneously, the total absorbance is a linear combination of the absorbances of the individual analytes:

$$A = \frac{1}{\ln(10)} \frac{d}{V} \sum_{i=1}^{n} \sigma_i N_i = \frac{1}{\ln(10)} \frac{d}{V} (\sigma_1 N_1 + \sigma_2 N_2 + \ldots + \sigma_n N_n) \quad \text{eq. 2}$$

In Eq. 2, n is the number of distinct species in the flow cell, $\sigma_i$ is the absorption cross section for molecule i, and $N_i$ is the amount of molecule i. Each individual absorbance spectrum has a different shape since each $\sigma_i$ does, so the shape of the measured absorbance spectrum can change if the relative amounts of the individual molecules vary. Therefore, if multiple types of molecules elute simultaneously or very close together in time, the shape of the measured absorbance is likely to vary over the course of the elution event. This fact can be used as a simple check for coelution. However, note that in the case of perfect coelution, where the relative amounts of the coeluting analytes remain constant, the shape of the absorbance spectrum will not change, although in general it will not be equal to the shape of any of the individual analyte absorbances.

The reference spectrum stored in the VUV reference library for a given molecule differs from the molecule's cross section only by a scaling factor. An absolute cross section can be obtained by determining the scaling factor using a variety of procedures. This step can be useful but isn't strictly necessary. Eq. 2 can be rewritten in terms of the individual molecules' reference spectra:

$$A = \sum_{i=1}^{n} f_i A_{i,ref} = (f_1 A_{1,ref} + f_2 A_{2,ref} + \ldots + f_n A_{n,ref}) \quad \text{eq. 3}$$

Where $A_{i,ref}$ is molecule i's wavelength-dependent reference spectrum and $f_i$ is a weighting factor, literally representing the ratio of the amount of analyte i contributing to the total absorbance spectrum to the amount of analyte i contributing to the analyte's reference spectrum.

A measured absorbance spectrum can be fit to a model defined by eq. 2 or eq. 3 using a regression procedure. In one exemplary embodiment, one such regression procedure is the general linear least squares procedure described in W.H. Press, S. A. Teukolsky, W. T. Vetterling, and B. P. Flannery, *Numerical Recipes in C: The Art of Scientific Computing, Second Edition*, Cambridge University Press, 1992. When applied to eq. 3, the $f_i$ are the parameters to be optimized by the fitting procedure and the $A_{i,ref}$ are the basis functions. Each of the absorbance spectra measured during an elution event are analyzed according to the general linear regression procedure, and the results for the optimized $f_i$ versus time become n distinct chromatographic responses. These responses are the baseline-resolved responses for the individual analytes. Each analyte's response can be quantified using peak height and/or area, if desired. It is noted that deconvolution done this way will work for perfectly coeluting species as well. A particularly useful representation of the deconvoluted chromatograms is obtained by integrating each of the reference spectra in eq. 3 according to one of the integration filters used to generate the original chromatogram. This results in an integration factor specific to each of the constituent analytes included in Eq. 3. Then, each $f_i$ multiplied by the analyte's integration factor is that analyte's contribution to the original response. In other words, the result is a true deconvolution of one of the chromatogram filters, which can be reconstructed by adding up all of the scaled $f_i$'s.

Figure 4:
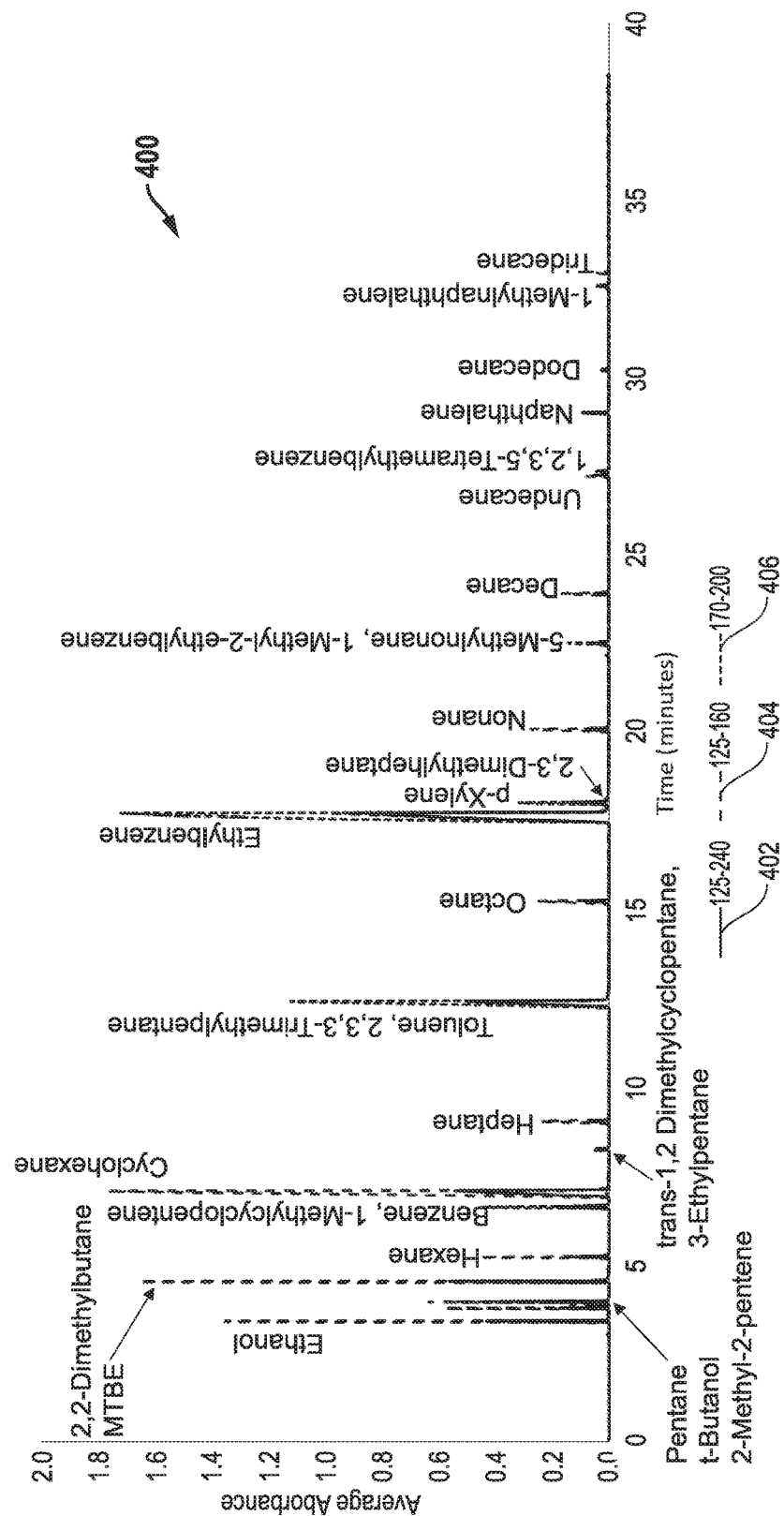
FIG. 4 illustrates a chromatogram for a standard nominally consisting of 29 components that occur in gasoline.

The potential for the rich dataset provided by GC-VUV to considerably simplify fuel analysis is illustrated in FIGS. 4 and 5. FIG. 4 shows an average absorbance versus time chromatogram 400 for a standard nominally consisting of 29 components that occur in gasoline. As shown in FIG. 4 specific wavelength regions, referred to herein as integration filters, of 125-240 nm 402, 125-160 nm 404 and 170-200 nm 406 are utilized. Included are several key coelutions that occur in gasoline analysis. One version of the DHA method uses a 100 m main column as well as a pre-column of slightly different phase in order to accomplish these separations. This 29 component sample is often used to "tune" a DHA setup by helping to optimize these separations, mainly by adjusting the properties of the pre-column. Using GC-VUV, none of the separations are necessary, because each of the coelutions can be deconvolved using VUV absorbance spectra. To emphasize this point, the separation shown in FIG. 4 was done using a 30 m column (no pre-column) and a faster temperature ramp than is typically employed in ASTM D6730, resulting in a significantly faster experiment.

Figure 5A:
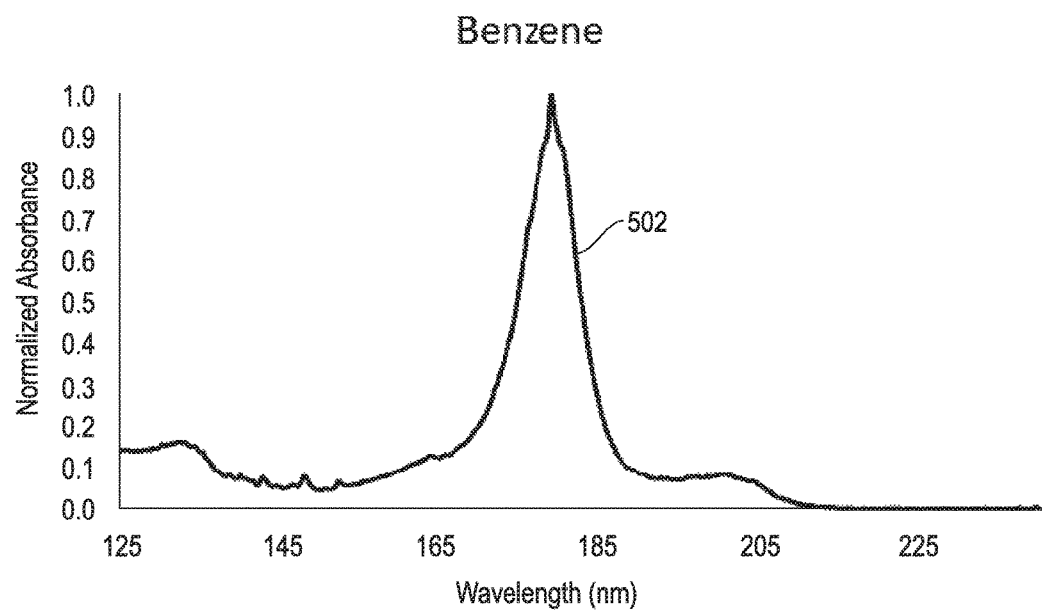
FIGS. 5a-5d illustrate the absorbance spectra for benzene and 1-methylcyclopentene.
Figure 5B:
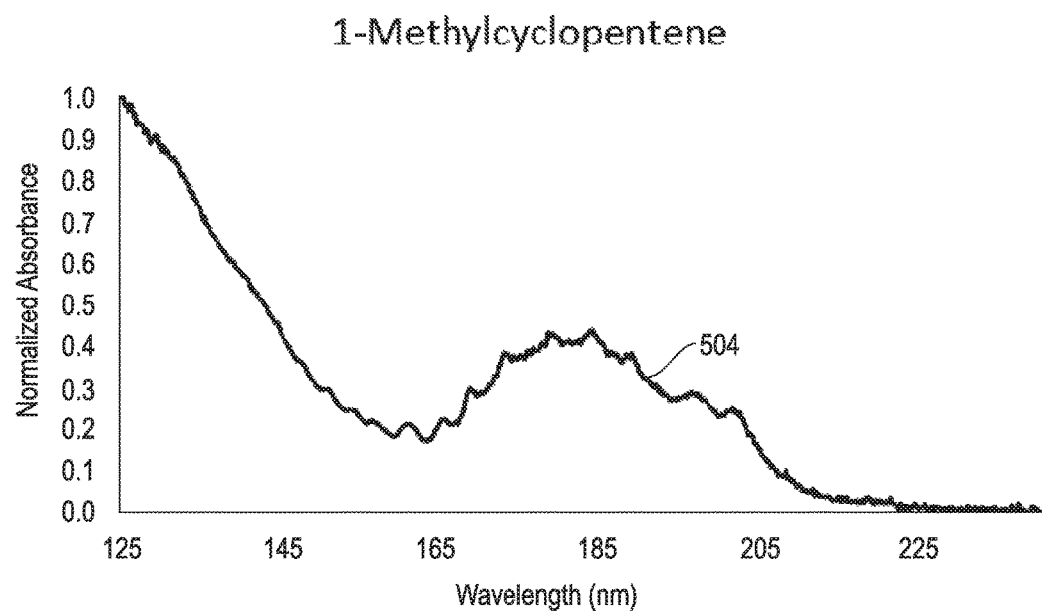
Figure 5C:
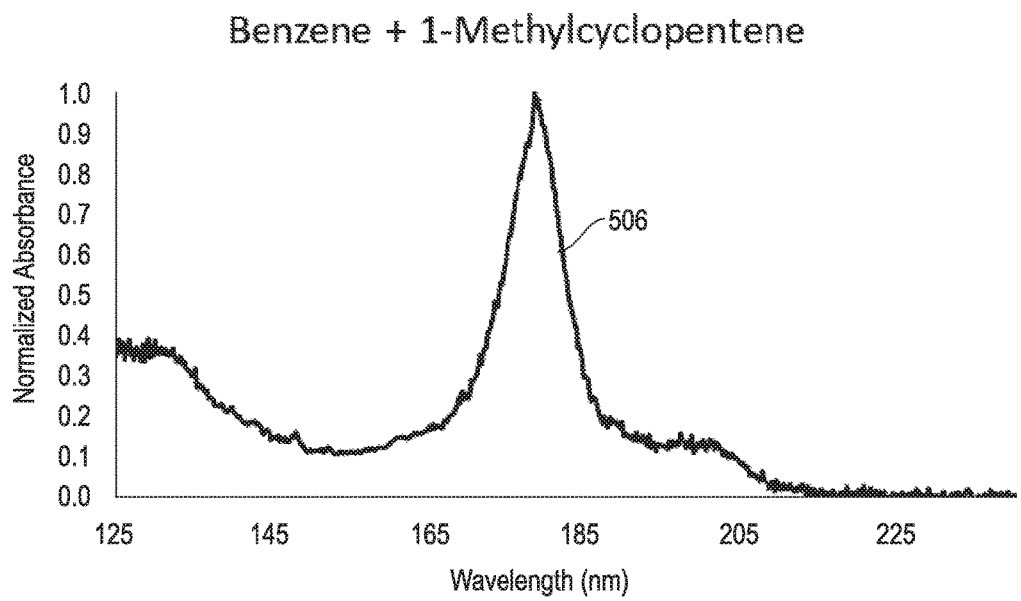
Figure 5D:
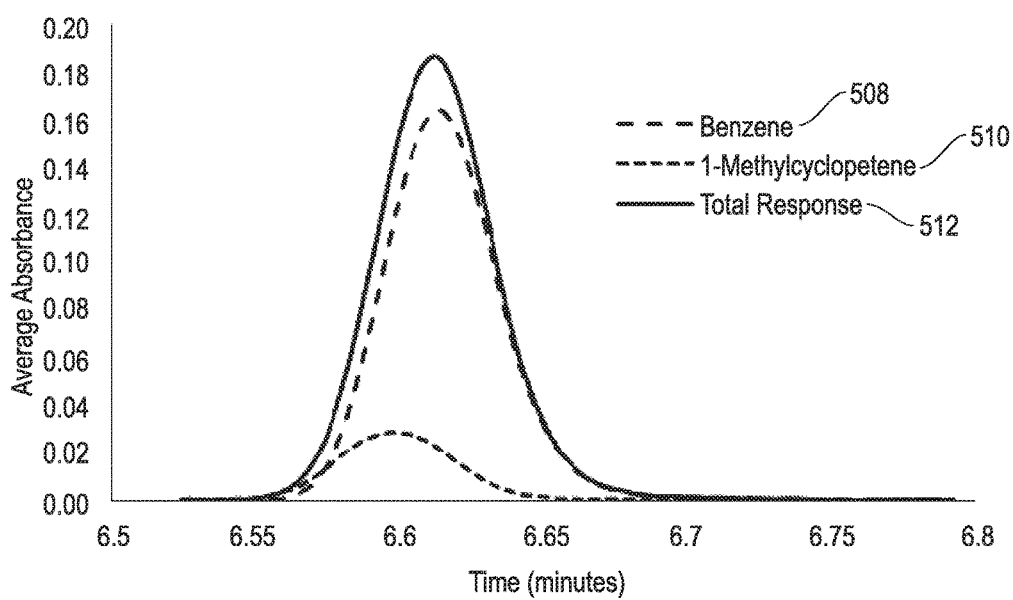

A specific example from the 29 component chromatogram is shown in FIGS. 5a-d for the case of benzene and 1-methylcyclopentene, which coelute at around 6.6 minutes. FIG. 5a shows the normalized reference spectrum for benzene 502. FIG. 5b shows the normalized reference spectrum for 1-methylcyclopentene 504. FIG. 5c shows an absorbance spectrum measured at a point on the benzene/1-methylcyclopentene peak 506. This absorbance spectrum is a linear combination of the benzene and 1-methylcyclopentene reference spectra, and is generally different in both magnitude and shape at each point in the chromatogram as the relative amounts of benzene and 1-methylcyclopentene in the flow cell vary. The deconvolution described above can be used to extract the relative amounts of benzene and 1-methylcyclopentene at each chromatogram point. This result is shown in FIG. 5d which shows the average absorbance versus time for benzene 508, 1-methylcyclopentene 510 and the total response 512. From FIG. 5d, it is seen that the individual responses from benzene 508 and 1-methylcyclopentene 510 have been baseline resolved, and there is no need to separate these compounds using the chromatography itself. Each constituent's elution time, peak height (maximum response), and peak area can be determined from the constituents' respective graphs.

In fact, every case of coelution in the separation shown in FIG. 4 can be deconvoluted this way. The potential to significantly shorten and simplify a chromatographic separation is clear: in order to fully resolve all 29 components using chromatography alone, a 100 m column and a ~1-3 m pre-column must be used, resulting in a ~2-3 hour separation and considerable setup time in order to "tune" the pre-column. When the VUV detector is used, a 30 m column is sufficient, and no pre-column is necessary. The resulting GC-VUV run time is about 35 minutes.

In one embodiment of the present disclosure, herein referred to as the "detailed" approach, the chromatogram is divided into multiple analysis windows. The analysis windows are set up ahead of time to include specific elution events. Each elution event consists of the elution of one or more molecular constituents from the original sample. For each window, a model is constructed (e.g., Eq. 3) that consists of a linear combination of the reference spectra for each of the molecular species that elute within the time window. During or after a GC-VUV run, a deconvolution is done using the model that was predefined for each of the windows. If all elution events are covered by analysis windows, the result is a baseline-resolved response peak for every component in the sample.

The creation of the time windows can be partially automated by preselecting chromatographic peaks from one or more of the chromatogram integration filters. Such peak integration techniques are known in the art. As used with regard to "peak integration," the term "integration" has a different meaning than it does for integration filters. Integration filters are integrations with respect to wavelength, while peak integration occurs with respect to time. Peak integration routines try to automatically determine distinct elution events by detecting response maxima, minima, and inflection points in a standard two-dimensional chromatogram. Various thresholds are set in order to determine when a peak has returned to baseline, or how to split two peaks that partially overlap. When the threshold criteria are met for a given chromatogram region, it is declared a peak, and the remaining part of the chromatogram integrated. Normally a peak height and area are estimated from the detected peaks, but for the present specification, only the distinct time regions associated with the determined peak events are used. The distinct time regions detected can be stepped-through manually or automatically and a deconvolution equation set up for each. A tiered search approach (described below) can be used to further automate the setup of the deconvolution for each analysis window by automatically detecting the identities of the eluting constituents.

It is important to note that once the deconvolution methods are set up for all of the time windows, subsequent chromatograms may be analyzed using the same window/deconvolution combinations, so the setup procedure only needs to be done once for a given set of experimental conditions.

Due to coelution, some of the baseline-resolved responses will actually overlap in time with each other, but because each response is separately determined by the deconvolution, each response peak can be individually processed to determine elution time, peak height, and peak area. A pre-determined calibration factor can be applied to either peak height or peak area to quantify the various compounds. Since the analytes' responses are baseline-resolved, an easy way to determine the peak area is to sum up the analyte's response over the associated analysis window. An analyte's response can in principle be divided across more than one analysis window, in which case the analyte's total peak area is the sum of its areas over the relevant windows.

It is noted that an analyte's "area" can consist of a summed response, but can also consist of a true area having units of absorbance multiplied by time. When using a simple sum to represent peak area, the areal magnitudes will depend on the detector scan rate, but this scan rate dependence falls out when doing relative quantitation.

It is further noted that the detailed method results in inherently more accurate determination of analyte peak areas than standard peak integration routines. This is due to the correct treatment of coelution. The present disclosure handles exact coelution as well as overlapping peaks. By contrast, standard peak integration routines cannot handle cases of perfect (or near perfect coelution), and only approximately find peak areas when peaks overlap.

In addition, the detailed GC-VUV method can potentially detect problems with the assumptions used in the analysis, since the quality of the linear fits depends on using correct reference spectra in the analysis windows. A goodness of fit metric, such as the $\chi^2$ or $R^2$ criteria, can be used to verify that the model adequately represents the measured absorbance spectra (the $\chi^2$ statistic is automatically generated during the linear fit procedure). If not, one or more of the compound identities may be wrong. A poor fit may also indicate that a problem with the experiment has caused the elution times to shift by a larger amount than the size of a typical analysis window, especially if the fits from multiple windows indicate poor agreement.

The fit metrics from individual fits can be combined to derive a fit metric for an entire analysis widow. The fit metrics for the analysis windows can be combined to derive a goodness of fit metric for an entire analysis. One way to do this is to simply average the fit metric for each individual fit to determine a fit metric for each analysis window. The fit metrics for the analysis windows can be further averaged to determine an overall goodness of fit for the analysis. A significant reduction in the quality of the analysis fit compared to prior, similar analyses can be an indication that a problem with the experimental procedure has occurred.

An exemplary method for processing the response peaks in order to determine relative concentrations of the components is now described. The relative mass or weight of an analyte, a, in a measured sample can be determined from $$M_a = 100 \times \frac{A_a \times RRF_a}{\sum_{i=1}^{n} A_i \times RRF_i} \qquad \text{eq. 4}$$

where $M_a$ is the mass % of analyte a, $A_a$ is the total response area measured in the experiment, and $RRF_a$ is the relative response factor for analyte a. The summation in the denominator occurs over all analytes present in the sample. The relative response factor takes into account the differences in per mass areal response for different compounds. For example, if the area response is determined from the average absorbance over the 125-240 nm wavelength region, a given mass of benzene results in a different area response than the same mass of iso-octane. The relative response factors can be determined experimentally using standards prepared with known relative amounts of analytes. If the relative mass, $M_2/M_1$ of two analytes in a standard is known and their relative areas measured using a GC-VUV experiment, the ratio of their relative response factors is given by $$\frac{RRF_2}{RRF_1} = \frac{M_2}{M_1} \cdot \frac{A_1}{A_2} \qquad \text{eq. 5}$$

If $RRF_1$ is known then eq. 5 can be solved for $RRF_2$. A specific compound is chosen (which one is arbitrary) to have an RRF of 1. Therefore, a series of standards can be used to determine RRF values for all of the compounds involved in an analysis. The RRF is a property of the molecule, so once it is determined, an RRF can be stored along with the molecule's reference spectrum in the VUV library. This means that a determination using a standard literally only needs to be done once for a given molecule, and the determined RRF can be used in any subsequent analysis thereafter. The only reason to modify the RRF is to refine it in the event that a better standard has been obtained.

The RRF does depend on the wavelength range associated with the chromatogram response used to obtain the response areas. If relative response factors are needed for a different wavelength region, the analyte's reference spectrum can be used along with the RRF for the analyte known for any wavelength region. This is because $$RRF_{region\ 2} = \frac{A_{ref,int,1}}{A_{ref,int,2}} \cdot RRF_{region\ 1} \qquad \text{eq. 6}$$

In eq. 6, $RRF_{region\ 1}$ and $RRF_{region\ 2}$ are the relative response factors for integration over wavelength regions 1 and 2, respectively, and $A_{ref,int,1}$ and $A_{ref,int,2}$ are the molecule's reference absorbance spectrum integrated over regions 1 and 2, respectively. Therefore, if a molecule's RRF associated with wavelength region 1 is known, that molecule's RRF associated with any other wavelength region can be determined from its reference spectrum. The various terms in eq. 4 can come from RRFs and peak areas associated with different wavelength regions, but the RRF and area used in each product term should be associated with the same wavelength region.

Many of the molecules in the VUV reference library have their absorbance cross sections calibrated. It is possible to determine the RRF appropriate for a given molecule relative to another molecule if the absorption cross sections of both molecules are known. In particular, to determine the RRF of a molecule, a, having a known cross section relative to methane, $$RRF_a = \frac{\Sigma_{methane}}{MW_{methane}} \times \frac{MW_a}{\Sigma_a} \qquad \text{eq. 7}$$

where $\Sigma_a$ is the absorption cross section for molecule a integrated over the associated wavelength region (e.g., 125-240 nm), $\Sigma_{methane}$ is the absorption cross section for methane integrated over the same wavelength region, and $MW_a$ and $MW_{methane}$ are the molecular weights of molecule a and methane, respectively.

The baseline-resolved peak areas and the RRFs for all of the molecules in the sample can be used along with eq. 4 to determine the relative mass % for all of the molecular species in the sample. The analytes' densities and molecular weights can be used to convert the mass % results to volume % or mole %.

The RRFs are very similar among species belonging to certain hydrocarbon classes, especially when the associated wavelength region is larger, for example 125-240 nm. Therefore, class-based RRFs are often useful, and multiple analytes belonging to the same class may use the same RRF.

The mass % results from the above analysis can be further grouped into mass % for specific classes of analytes. In this way, the first embodiment can be used to do class-based analysis as well. For example, when analyzing unleaded gasoline, the mass % results for all constituents belonging to the paraffins group can be summed, giving the total mass % for paraffins. The same can be done for isoparaffins, and so on for each of the PIONA classes. In this way, a full PIONA analysis can be obtained from a measurement using the detailed approach.

Further aspects of the detailed approach will be discussed later in the specification.

Figure 6A:
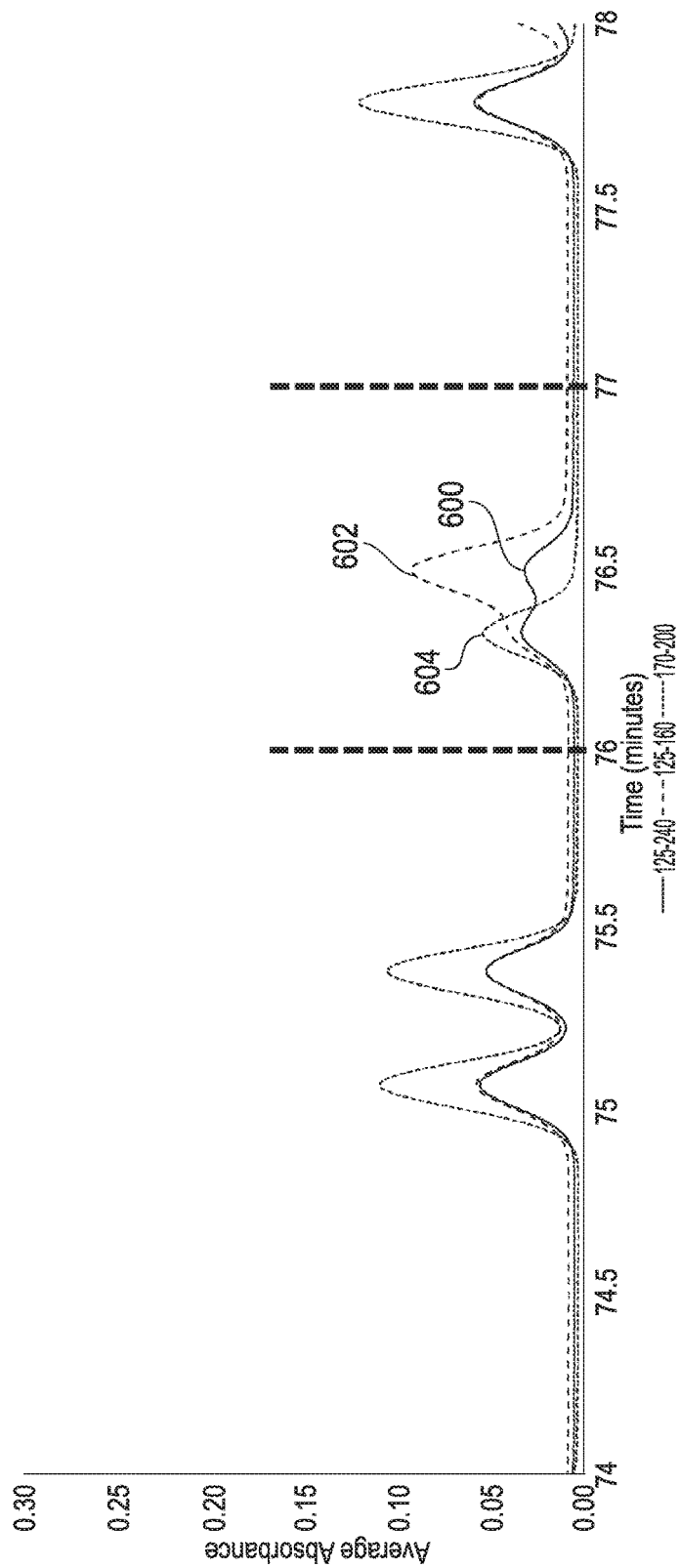
FIG. 6a illustrates a section of a GC-VUV separation of a 139 component PIONA standard.
Figure 6B:
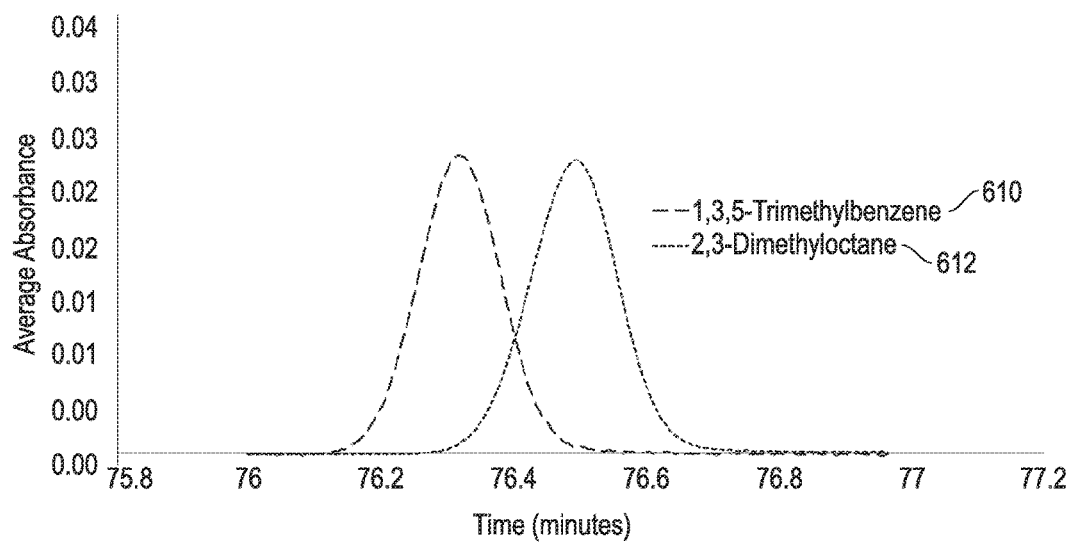
FIG. 6b illustrates a deconvolution of the 76-77 minute region for 1,3,5-trimethylbenzene and 2,3-dimethyloctane.

In describing the classification approach, a brief illustration of a key concept is helpful. FIG. 6a shows an average absorbance versus time graph for a section of a GC-VUV separation of a 139 component PIONA standard for wavelength filters 125-240 nm (graph 600), 125-160 nm (graph 602) and 170-200 nm (graph 604). The molecules 1,3,5-trimethylbenzene and 2,3-dimethyloctane partially coelute at about 76.5 minutes. A deconvolution of the 76-77 minute region using the reference spectra for 1,3,5-trimethylbenzene 610 and 2,3-dimethyloctane 612 is shown in the average absorbance versus time graph of FIG. 6b. The reference spectra were integrated using the 125-240 nm filter, and the peak areas of the 125-240 nm response for each analyte were calculated by summing the scaled weighting factors ($f_i$ multiplied by the integration factors) across the 76-77 minute region for each analyte. The results (in absorbance units, AU) are 0.9418 for 1,3,5-trimethylbenzene and 0.9962 for 2,3-dimethyloctane.

Figure 6C:
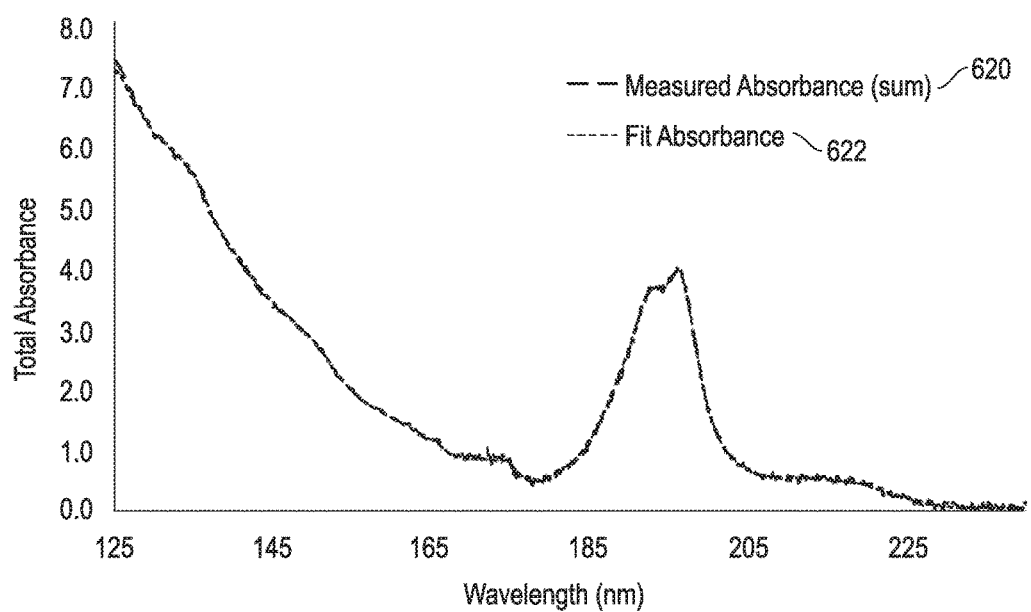
FIG. 6c illustrates a measured absorbance sum and fit absorbance for the components of FIG. 6b.

FIG. 6c shows total absorbance versus wavelength for a single absorbance spectrum 620 obtained by summing all of the absorbance scans between 76 and 77 minutes on a wavelength-by-wavelength basis. Since each individual absorbance spectrum is a linear combination of the 1,3,5-trimethylbenzene and 2,3-dimethyloctane reference spectra, the resulting total absorbance spectrum is also a linear combination of the same two reference spectra. FIG. 6c also shows a fit spectrum 622 that results from a linear fit using Eq. 3 for two components, the two components again being the 1,3,5-trimethylbenzene and 2,3-dimethyloctane reference spectra. If these two spectra are again integrated using a 125-240 nm filter, the scaled optimized fit weights are equal to the peak areas obtained above via the deconvolution procedure, i.e., 0.9418 for 1,3,5-trimethylbenzene and 0.9962 for 2,3-dimethyloctane. This is a general property of the absorbance from a chromatographic separation: finding the optimized fit weights for the individual spectra and then summing them yields an identical result to finding the optimized fit weights of the summed total absorbance. The average of the absorbances within the time window could also be fit, in which case the result is the average of the fit weights of the individual spectra.

It is noted that in the above example (and in general) it does not matter how the analytes are distributed across the time window. It also doesn't matter if the contributions from the analytes are entirely contained within the time window. For instance, in the above example the time window could be divided into two windows, one from 76-76.5 minutes (window 1) and a second from 76.5-77 minutes (window 2). Fits of total absorbance from each of windows 1 and 2 can be done, in each case using the two-component model described above. The total peak area for 1,3,5-trimethylbenzene is the sum of the results for 1,3,5-trimethylbenzene from both windows. Likewise, the total peak area for 2,3-dimethyloctane is the sum of the 2,3-dimethyloctane results from the two windows.

As before, "area" refers to the summed response over the time window, not a true geometric area with units of absorbance units multiplied by time. This is not a limitation, however, since a true geometric area could also be used with the same conclusions.

In one embodiment of the classification approach, a chromatogram is integrated by dividing the chromatogram into equal time slices and fitting the total absorbance spectrum for each slice to Eq. 3, using appropriate reference spectra for the $A_{ref,i}$. The result is the contribution from each component to the total response of the slice. The total contribution of each constituent to the chromatogram is obtained by summing the contribution that component made to each of the individual windows.

It is conceivable that a model of the entire library of available reference spectra could be fit to the total absorbance of a time window. In principle, only the compounds that contribute significantly to the total absorbance would yield significant weights, the rest would essentially be zero. In practice, how well this would work depends on how many compounds contribute and which compounds they are. A combination of a large number of similar compounds is likely to yield ambiguous results. Also, the computational expense of such a calculation is large. At any rate, it should never be necessary to try to fit a large number of reference analytes to a given total absorbance spectrum.

In some cases, there may only be a few compounds in the sample being analyzed. In such cases, a subset of the VUV reference library can be preselected, and only molecules in the list considered as candidate reference spectra. Many other selection constraints can be employed, including but by no means limited to knowledge of the general class of molecules present, or knowledge of their atomic makeup.

A particularly powerful selection constraint is the use of retention time, just as in the case of GC-FID. However, when using GC-VUV, the retention times do not need to be accurately known. In one implementation, a retention time window can be predefined, and at each time slice a subset of the VUV library is selected based on analytes known to elute within the given retention time window.

Retention indices are particularly useful for this purpose, since they provide a relative elution order that does not depend on column length, column diameter, or flow rate. Retention indices are well-known in the art. Typically, a value is assigned to each molecule that ranks the molecule's retention order relative to the retention times of the linear alkanes (a.k.a. paraffins). Each linear alkane is given an RI value according to the number of carbon atoms in the molecule. For example, pentane has an RI of 500, hexane of 600, decane of 1000, etc. A molecule that elutes between heptane and octane has a retention index between 700 and 800, as determined by experiment. For example, when using a standard nonpolar capillary column, toluene has a retention index of about 750, and elutes roughly half-way between heptane and octane. The retention order depends on the type of chromatography and especially the phase of the column, but otherwise is insensitive to the length of column and carrier gas flow rate. For given values of any of these conditions, a sample consisting of the linear alkanes is run to determine the linear alkane retention times. This gives the specific retention times corresponding to RI values of 500, 600, 700, etc. Another molecule's retention time can then be predicted from its experimentally determined retention index and interpolation between the linear alkane retention times/indices. Conversely, an eluting analyte's retention index can be determined from its retention time and interpolation between the linear alkane retention times/indices. For isothermal conditions, a logarithmic interpolation is used. The interpolation is linear when temperature programmed chromatography is used. Retention indices for each of the compounds are typically stored in a library along with other compound-specific information. Each compound may be associated with multiple retention indices relevant to different separation conditions, and especially dependent on column stationary phase.

Retention indices are heavily used in GC-FID methods such as ASTM D6730. However, in the case of GC-FID, retention times/indices are the only method for identification, and as a consequence they have to be very accurately known. In addition, elution times and elution orders have to be strictly controlled from run to run as very little variation can be tolerated. In the specification for ASTM D6730, suggested retention index windows start at +/−15 for the earliest elution times where very few compounds elute, but that window size very quickly decreases to +/2.6 for RI of 300-400, and further to +/−0.6 for RI values of 500 or greater. Any variation of equivalent retention times greater than this is likely to result in peak misidentification and cause errors in the final analysis results. When using the conditions described in ASTM D6730, in the vicinity of pentane (RI=500) an RI window of 1.2 corresponds to about 4 seconds. By contrast, the GC-VUV method described below typically uses RI windows of +/−25 or more, which can easily accommodate run-to-run variations in elution time. An RI window of that size is able to tolerate moderate variations in retention order as well. Retention indices are stored in the VUV reference library along with the various analytes' reference spectra, molecular weight, and other properties.

Figure 7:
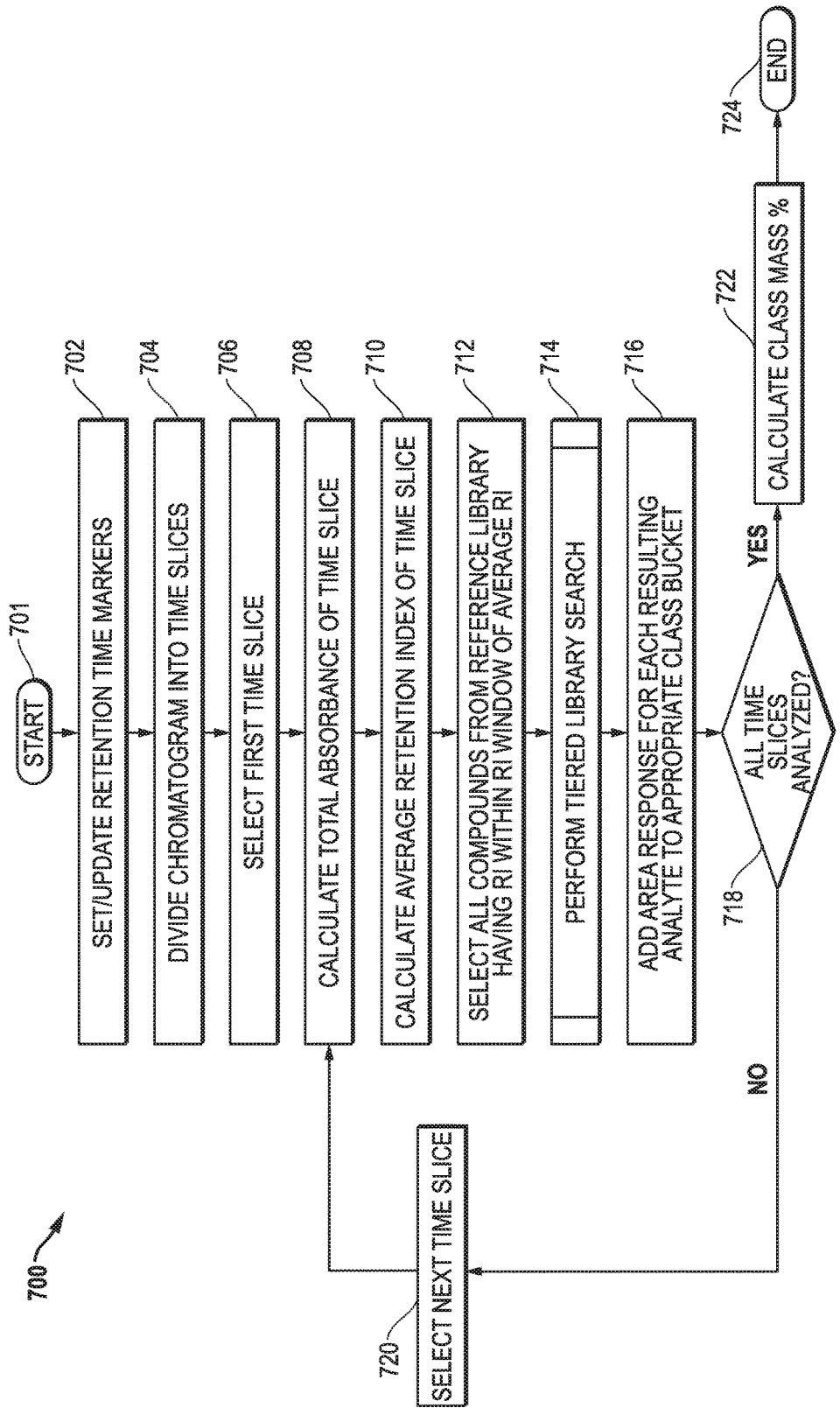
FIG. 7 illustrates a work flow chart for one exemplary embodiment of a classification analysis technique.
Figure 8:
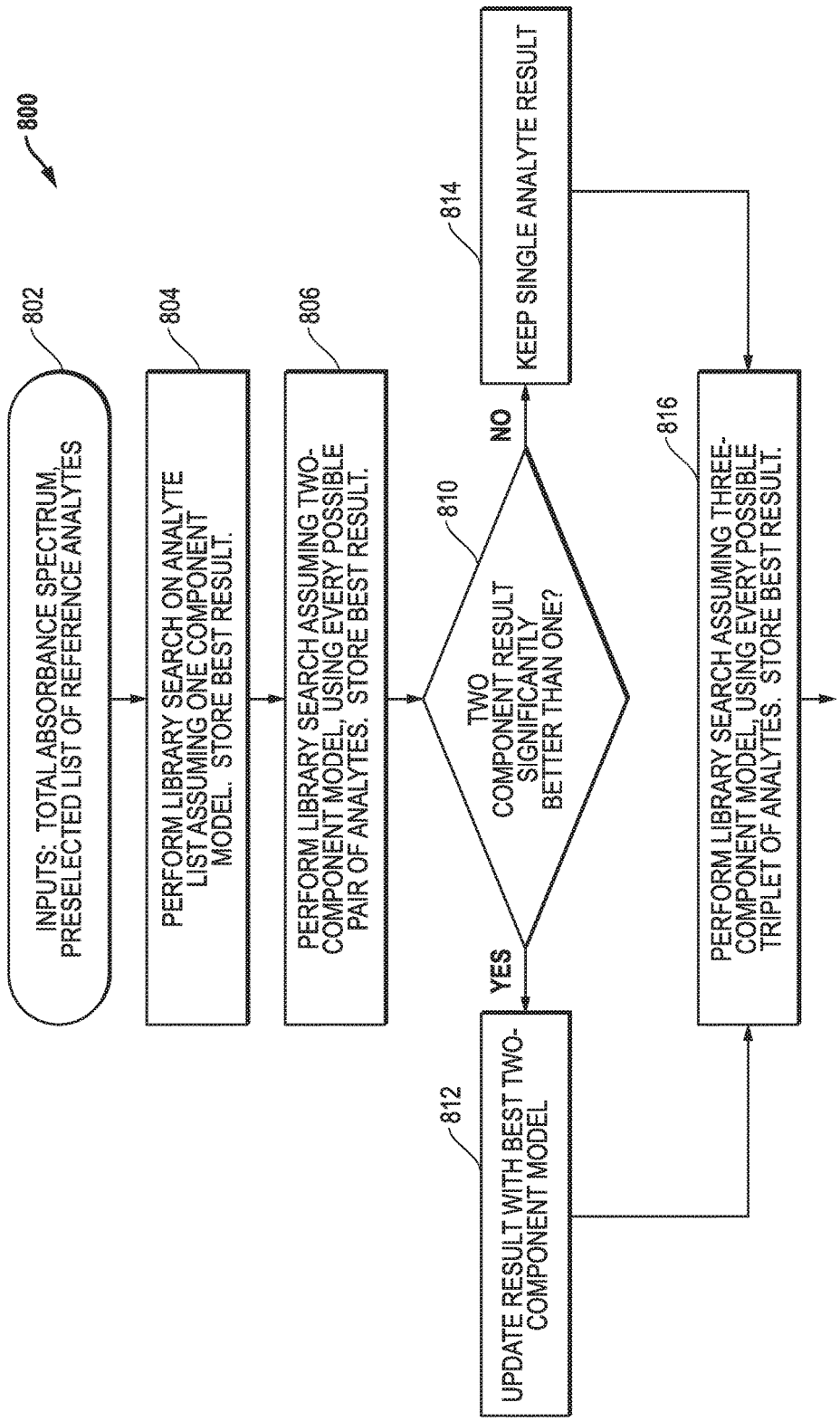
FIG. 8 illustrates an exemplary work flow for performing a tiered library search for use with the work flow of FIG. 7.

A specific embodiment of the classification analysis is now described and illustrated by a flow diagram 700 in FIG. 7. Also Included is a description of a method for determining appropriate reference spectra to use for each time slice, illustrated by a flow diagram 800 in FIG. 8. As shown in FIG. 7, the flow starts at step 701. First, a set of compounds are selected to serve as retention time markers at step 702 ("set/update retention time markers"). The analytes can be the set of linear alkanes run under the same conditions as the sample being analyzed. However, a particularly advantageous embodiment of the present disclosure uses compounds easily identifiable in the measured sample itself. In analysis of gasoline, linear alkanes may be used for the early part of the chromatogram where very few compounds elute. In the middle and later parts of the chromatogram, aromatic compounds such as benzene, toluene, o-xylene, naphthalene, and 1- and 2-methylnaphthalene are very easy to pick out based on their measured spectra, even though they typically coelute with other compounds. Therefore, one embodiment simply identifies the retention times of a list of 10-12 easily identified analytes, and uses their experimental retention indices to determine the retention index corresponding to every other elution time in the chromatogram. For typical temperature ramps, a linear interpolation is sufficient to do this, although for slow temperature ramps a log-based interpolation can be used. A GC-VUV method can use multiple types of interpolation as the oven ramp conditions change, but one embodiment advantageously uses a linear interpolation throughout. Once a GC-VUV method and retention time markers are set, subsequent experiments using the same GC-VUV run parameters can typically continue to use the same retention time markers. However, an automated method for updating retention time markers will be discussed further below.

After setting the retention time markers, the chromatogram is divided into time windows/slices at step 704 ("divide chromatogram into time slices"). The slices don't have to be of equal size, but in one embodiment the time slices are of equal size and the product of the slice size and the number of slices equals the total chromatogram time. At step 706 ("select first time slice") a time slice is selected. At step 708 the total absorbance of a time slice is calculated by summing the individual absorbance spectra from the time slice. Then at step 710 the average retention index of a slice is calculated. More particularly, from the average time within each slice, t, calculate $$RI = RI_i + \frac{RI_{i+1} - RI_i}{t_{i+1} - t_i}(t - t_i) \quad \text{Eq. 8}$$

for the average RI associated with the time slice. In Eq. 8, $RI_i$ is the retention index of the elution time marker preceding the current slice, $RI_{i+1}$ is the retention index of the next marker that elutes after the current slice, $t_i$ is the elution time of the marker preceding the current slice, and $t_{i+1}$ is the elution time of the next marker that elutes after the current slice. Note that $t_i$ and $t_{i+1}$ do not have to be directly determined from the chromatogram being analyzed. Determination of the $t_i$'s of the retention time markers can occur once for a given set of GC conditions, and are generally close enough to provide accurate results for subsequent runs. Nevertheless, more accurate retention indices can result from determination of the $t_i$ from the actual chromatogram being analyzed, as will be described in more detail later.

An alternative to Eq. 8 for the case of isothermal GC conditions or very slow oven ramps is given by $$RI = RI_i + \frac{RI_{i+1} - RI_i}{\log t'_{i+1} - \log t'_i}(\log t' - \log t'_i) \quad \text{Eq. 9}$$

where $RI_i$ is the retention index of the elution time marker preceding the current time or time slice, $RI_{i+1}$ is the retention index of the next marker that elutes after the current time slice. t' is the adjusted retention time, defined by $t'=t-t_0$ where t is the retention time and $t_0$ is the retention time of an un-retained compound, i.e., a compound unaffected by the column phase. $t_i'$ is the adjusted retention time of the marker preceding the current slice, and $t_{i+1}'$ is the adjusted retention time of the next marker that elutes after the current slice. Under some conditions use of absolute retention times instead of the adjusted retention times may provide accurate enough retention indices.

In general, GC-VUV retention indices do not need to be particularly accurate, and a linear interpolation can usually be used throughout a GC separation, even one involving isothermal steps. However, if more accurate retention index determination is desired, linear and log-based interpolation can be combined in cases where a significant isothermal or slow oven ramp portion are present, such as in the case of a long initial temperature hold program. For a separation occurring under strictly isothermal conditions, the log-based interpolation given in Eq. 9 should be considered.

Next, at step 712 ("select all compounds from reference library having RI within RI window of average RI"), a subset of the VUV reference library is selected using the retention index of the time slice. The analyte list is generated by selecting all molecules in the library having retention indices within a preset range of the RI determined for the time slice. The RI range used can be different at different parts of the chromatogram. However, for many gasoline analysis, a fixed RI range of +/−25 has been successfully used (this is referred to as the "RI window" in FIG. 7). This reduction of the analyte list can be done in conjunction with other constraints. For example, for fuel analysis, a reduced reference library may be pre-generated from the main VUV reference library by only considering molecules that occur in petroleum products. Similar analysis-specific libraries can be defined for other types of complex analysis.

Next at step 714 a tiered library search is performed. The total absorbance spectrum constructed in step 708 is fit using a tiered search, illustrated in more detail by the flow diagram 800 in FIG. 8. The inputs 802 to flow diagram 800 are total absorbance spectrum and a preselected list of reference analytes. The first step of the flow diagram 800 is step 804: "Perform library search on analyte list assuming one component model. Store best result." Thus, the first step of the tiered search fits the total absorbance spectrum using Eq. 3 for one component. The fit is performed for each analyte in the reduced analyte list by replacing $A_{1,ref}$ with the analyte's reference spectrum. This results in one fit for each reference analyte in the reduced list. A fit metric such as the chi-square, $\chi^2$, coefficient of determination, $R^2$, or any number of other fit criteria known in the art is associated with each of the fits, and the analytes in the list are ordered according to best result. The procedure of fitting each reference spectrum to the total absorbance spectrum is referred to as a "library search" in FIG. 8, although the "library" in this case is only a subset of the full VUV reference library.

The second step of the tiered search is step 806: "Perform library search assuming two-component model, using every possible pair of analytes. Store best result." Thus, the second step of the tiered search again fits the total absorbance spectrum, but this time using Eq. 3 in two-component form. In each fit, $A_{1,ref}$ and $A_{2,ref}$ are replaced with one possible pair of reference spectra from the reduced analyte list. Since there is no need to consider cases where $A_{1,ref}$ and $A_{2,ref}$ are the same compound or combinations that differ only in the reversal of $A_{1,ref}$ and $A_{2,ref}$, the number of fits required is given by the binomial formula. For a reduced analyte list size of n, a total of $$\frac{n!}{2(n-2)!}$$

fits are performed. Again, the fit results are ranked according to a fit metric and the best two-component result compared to the best fit from the one-component search. Then at step 810 ("two component result significantly better than one?") a comparison is performed. If the ranking metric for two-component search is significantly improved over the ranking metric for the one-component search, the overall result for the time window is updated to the best two-component result as shown by step 812 ("update result with best two component model"). If not, then the best one-component result remains the best candidate for the time window as shown by step 814 ("keep single analyte result").

Then step 816 may be performed if desired: "Perform library search assuming three-component model, using every possible triplet of analytes. Store best result." In this step a three-component model is assumed, and every possible triplet (without repetitions) is considered, leading to $$\frac{n!}{6(n-3)!}$$

total fits. Though not shown in the flow diagram similar to steps 810, 812, and 814, the best fit from this stage (step 816) is compared to the best candidate fit from the prior two stages, and if a significant improvement to the ranking metric has been achieved, the result is updated to the best three-component result. Otherwise, the previous best result is retained.

This procedure can be iterated to combinations of 4- and 5-components, etc. to whatever extent is desired. However, the number of possible combinations that must be fit rapidly increases with n, and quickly becomes intractable. Additionally, the number of compounds that can be simultaneously fit and yield reliable results is limited, although this limit depends strongly on how distinct the various reference spectra are. In one particularly advantageous embodiment, a limit of three possible coelutions is enforced, and the experimental and analytical conditions adjusted to ensure this condition is met practically. The two most common conditions to adjust are the speed of the GC separation and the size of the analysis time window. Either condition can be adjusted for an entire run or can vary throughout a run, if desired.

As an alternative to placing a hard constraint on the total number of coelutions considered, a stopping condition can be applied and the algorithm iterated, successively increasing the number of possible coelutions n, until the stopping condition is met. In this case, it is possible that each time slice may ultimately test a different maximum number of coeluting analytes.

Additional criteria can be applied at this stage. For example, a threshold value for the fit metric may be enforced, and a result that does not meet the threshold flagged as such. In one embodiment, a time slice not meeting a fit criteria after the tiered search is flagged as "unknown". A further criteria may consist of reconstructing the total response from the tiered search results and requiring that it equal the original measured response to within some threshold. This criteria can be applied to any number of responses generated through different integration filters.

The final result of the tiered search procedure is the simplest model that fully explains the measured total absorbance spectrum of the analyzed time slice. This model is a prediction of the number of coeluting compounds along with the most likely candidates for their identities. The tiered search procedure also produces the optimal fit weights of each analyte. If the reference spectra are integrated according to a particular filter, the optimal fit weights multiplied by these integration factors are the contributions of each of the best-fit analytes to the total response in the time slice corresponding to the same integration filter. Even though the tiered search is shown embedded within the classification approach in FIG. 7, it can also stand by itself. The time slice can be a manually selected time window, and the total or average absorbance calculated from the absorbance scans within the time window. The list of analytes provided can consist of the entire reference library or a reduced analyte list constrained by retention time or any number of other constraints. In this way, the stand-alone tiered search functions as an advanced library search, capable of discovering the identities of multiple compounds within a time window.

Returning to FIG. 7, the next step after the tiered search is to bin the analytes' contributions to the response in the time slice according to their analyte classes at step 716 ("add area response for each resulting analyte to appropriate class bucket"). As each time slice is analyzed, a running total of each of the detected molecules' contributions to the slice response areas is maintained. In this way, an analyte's total peak area response is determined even if it is distributed over multiple analysis windows. Other aspects of the analysis results may be similarly binned. For example, the analysis can keep track of the total contribution from various classes of molecules. In the case of gasoline analysis, a total area for each of the five PIONA classes is maintained as the analysis progresses. For example, if the analysis of a particular time slice yields 1-pentene with a slice area of 0.3 AU, 0.3 AU is added to the total area of the olefins group. If the analysis of another time slice yields 1,3,5-trimethylbenzne at 0.9418 AU and 2,3-dimethyloctane at 0.9962 AU, 0.9418 AU is added to the total aromatics area and 0.9962 AU is added to the total isoparaffins area.

The procedure is iterated until all time slices have been analyzed as shown by steps 718 ("all time slices analyzed") and step 720 ("select next time slice"). The result of analyzing the entire chromatogram is the total response area for each of the molecular classes, in addition to the total response areas from any specific molecular constituents of interest. The relative mass percent of each class can then be calculated at step 722, for example by use of relative response factors (e.g., via Eq. 4). A myriad of other quantities can be calculated, such as the density, boiling point, and effective octane rating in the case of unleaded gasoline.

It will be recognized that in one embodiment a feature of the techniques described herein is the fact that individual species or class response areas are obtained in an automated fashion and under conditions that can include significant coelutions. There are a variety of ways to do the quantitation after that, one in particular being the application of relative response factors to determine mass % and volume % (as discussed herein). A traditional calibration methodology can also be applied: basically determining a slope/offset conversion between peak areas or heights and sample concentration ahead of time, often by using prepared standards, and then apply this calibration factor to individual species or class areas/heights when performing measurements of unknown samples. Thus, a traditional (e.g., simple slope/offset) calibration factor can be applied to any of the peak response areas determined via the classification approach as well.

It will also be recognized that in either the detailed or classification approach only a subset of the chromatogram needs to be analyzed if only part of the sample is of interest.

Figure 9:
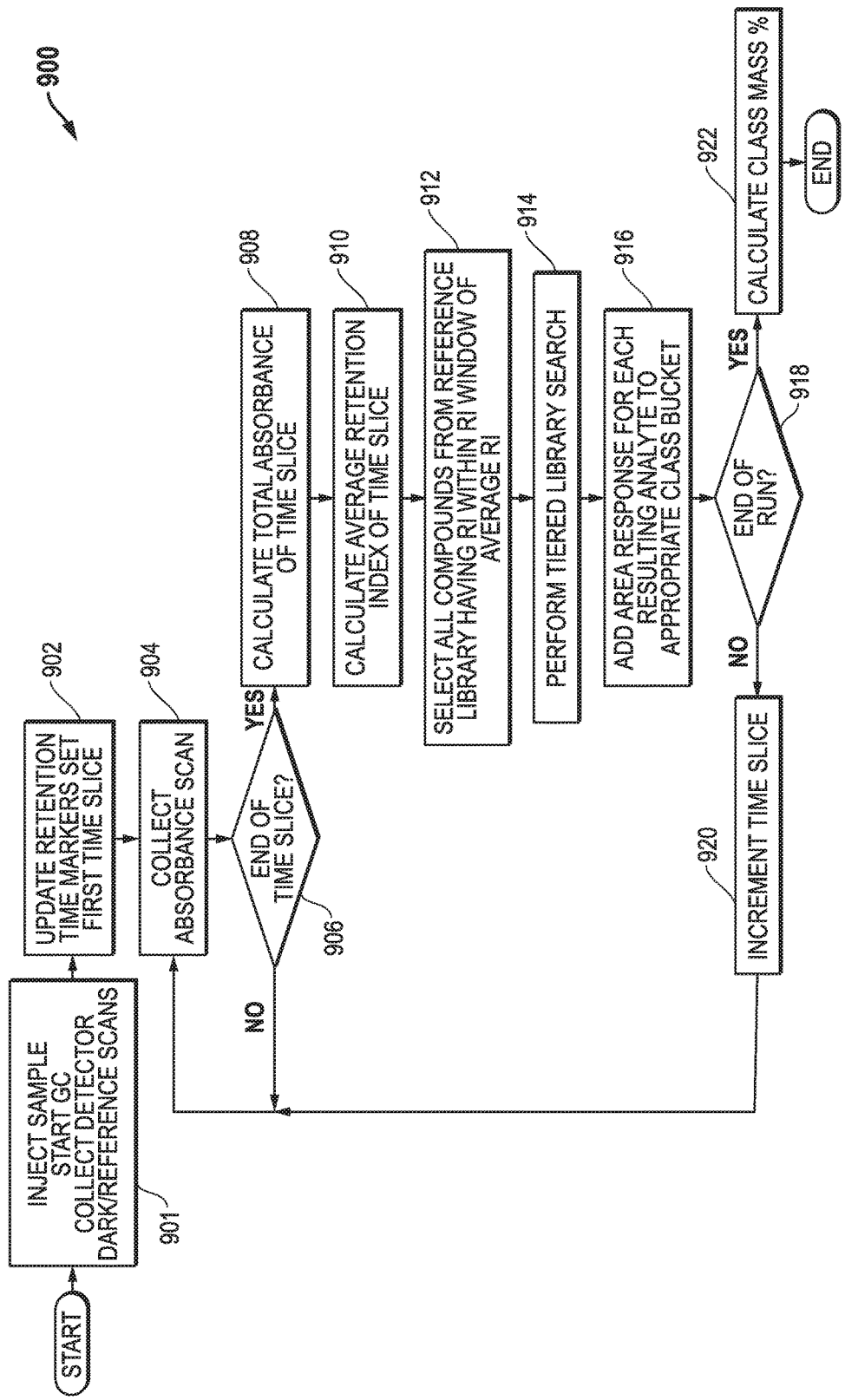
FIG. 9 illustrates another work flow chart for another exemplary embodiment of a classification analysis technique.

FIG. 9 shows a flow diagram 900 illustrating a second implementation of the classification method, where the time slice analysis is done in real-time as the absorbance data is obtained, with a minimum of post processing. The measurement begins with sample injection and starting the GC and detector at step 901 ("inject sample, start GC, collect detector, dark/reference scans"). The GC implements its preprogrammed temperature ramp. Meanwhile, the detector performs a dark scan and reference scan and begins to collect absorbance scans according to the preset scan settings. Then step 902 ("update retention markers, set first time slice") is performed. Thus, criteria for selecting time slices are initiated, and the times corresponding to the first time slice determined. Retention time markers are updated, usually by loading them from a file associated with the run method.

Then at step 904 absorbance scans are collected until the end of the first time slice is encountered as indicated by step 906 ("End of time slice?"). At step 908 the total absorbance of the time slice is calculated and at step 910 the average retention index associated with the time slice is calculated. Next step 912 ("select all compounds from reference library having RI within RI window of average RI") is performed. Here, a list of analytes falling within a predefined window of the time slice is generated. Then at step 914 a tiered library search is performed using the total absorbance and the reduced list of analytes. Step 916 then occurs ("add area response for each resulting analyte to appropriate class bucket"). Here, the area response results of the time slice analysis are binned according to analyte class or individual species as predefined in the method. At step 918 it is determined if the end of the run has been reached. If the end of the run has not been encountered, then the procedure continues to step 920 to increment the time slice and then to step 904 for more data collection. The relative mass percent of each class can then be calculated at step 922.

Note that with the use of modern multi-tasking operating systems, the absorbance data collection for the next time slice can proceed in parallel with the tiered search and processing of the current time slice. The analysis of each time slice is typically very fast, but it is possible for the analysis to lag the data collection, a condition that could be represented by a modification of the FIG. 9 flow diagram. In fact, there are multiple variations of the method flows shown in FIGS. 7-9 that can produce equivalent results. Generally, it is desirable to meet two conditions—the raw absorbance data for a given time slice has to be available before the time slice data can be processed, and the entire chromatogram must be processed before the final bulk properties of the sample can be calculated, although even this last condition may not need to be strictly met in all circumstances.

As mentioned previously, it is often the case that classification analysis is all that is desired. In this case, the class similarity of absorbance spectra illustrated earlier often means that it is not necessary to have every molecular constituent in a sample pre-characterized by a reference spectrum. If a molecular constituent is present in the sample, but its reference spectrum is not in the VUV reference library, the next most probable outcome of a library search is often another molecule's reference spectrum within the same class. As long as there is some class representation of an unknown molecule in the reference library, that representation can be used as an approximate characterization of the molecule's response.

The result is that in order to determine the total response areas for analyte classes in a complex sample, the need for reference characterization of every molecular constituent is replaced with the need for "sufficient" representation of each class in the reference library. Sufficient representation can vary depending on what the molecular constituents are and may require experimentation. As a starting point, it is certainly desirable to have as many specific constituents as possible pre-characterized by their reference spectra. In analysis of organic samples, the number of carbon atoms in a molecule (i.e., its carbon number) is a convenient subclassification within hydrocarbon class. Instead of constructing a specific reference spectrum for every molecular constituent of a given class and carbon number, a smaller, representative set of reference spectra is generated from reference characterization of several of the molecules belonging to that class and carbon number. A molecular constituent that is not included as a specific reference spectrum in the VUV reference library is represented by the closest existing reference spectrum of the same class and carbon number, or by a linear combination of multiple reference spectra from that class and carbon number. In this way, the representative set for each class and carbon number functions as a basis set for all analytes of that class and carbon number.

Note that there is a strong correlation between carbon number and boiling point within a given hydrocarbon class. This means that molecular constituents of the same class and with similar carbon numbers elute near each other when using standard nonpolar capillary chromatography, especially under conditions where the phase separation provided by the analytical column is relatively weak.

Additionally, the basis reference spectra can themselves be linear combinations of other reference spectra of the same analyte class. All of this substantially reduces the burden of reference characterization, since useful class-based reference spectra can come from experiments where the analytes' identities are not necessarily known, or where molecular species may not be well-separated from other members of the same class.

In many cases, representative samples of the type to be analyzed can be used to generate the reference basis sets. One embodiment of the present disclosure is to run faster separations with more coelution than would be possible using other GC detectors. Since reference characterization only needs to be done once, more detailed separations using longer columns and slower temperature ramps can be done for the purpose of generating reference basis sets. The sample properties and/or spectral characteristics of the absorbance scans can be used to identify class-based reference spectra, and the elution time used to discern the associated carbon number. In a further specific embodiment, a DHA-type separation can be performed on a matrix of liquid fuel samples specifically for the purpose of generating a reference basis set useful for faster GC-VUV measurements of other similar samples.

In the case of petroleum analysis, the number of lower carbon-number (C1-C7) constituents is small enough that characterizing nearly all of the constituents is tractable. Suitable standards exist for many of the low carbon number components, and more thorough separations can be done on gasoline and naphtha samples for the purpose of obtaining specific molecular reference spectra. As the carbon number increases, the number of possible molecular constituents increases rapidly, and analyte-specific separation becomes more difficult. Gasoline production streams rich in specific hydrocarbon classes can be used for the purpose of obtaining reference spectra at these higher carbon numbers. For example, a reformate stream has a heavy aromatic content, and careful GC separation of a sample from such a stream produces regions of the chromatogram consisting only of aromatics. This is especially useful in the C10-C12 region, where a lot of aromatics occur but standards are harder to come by.

Figure 10:
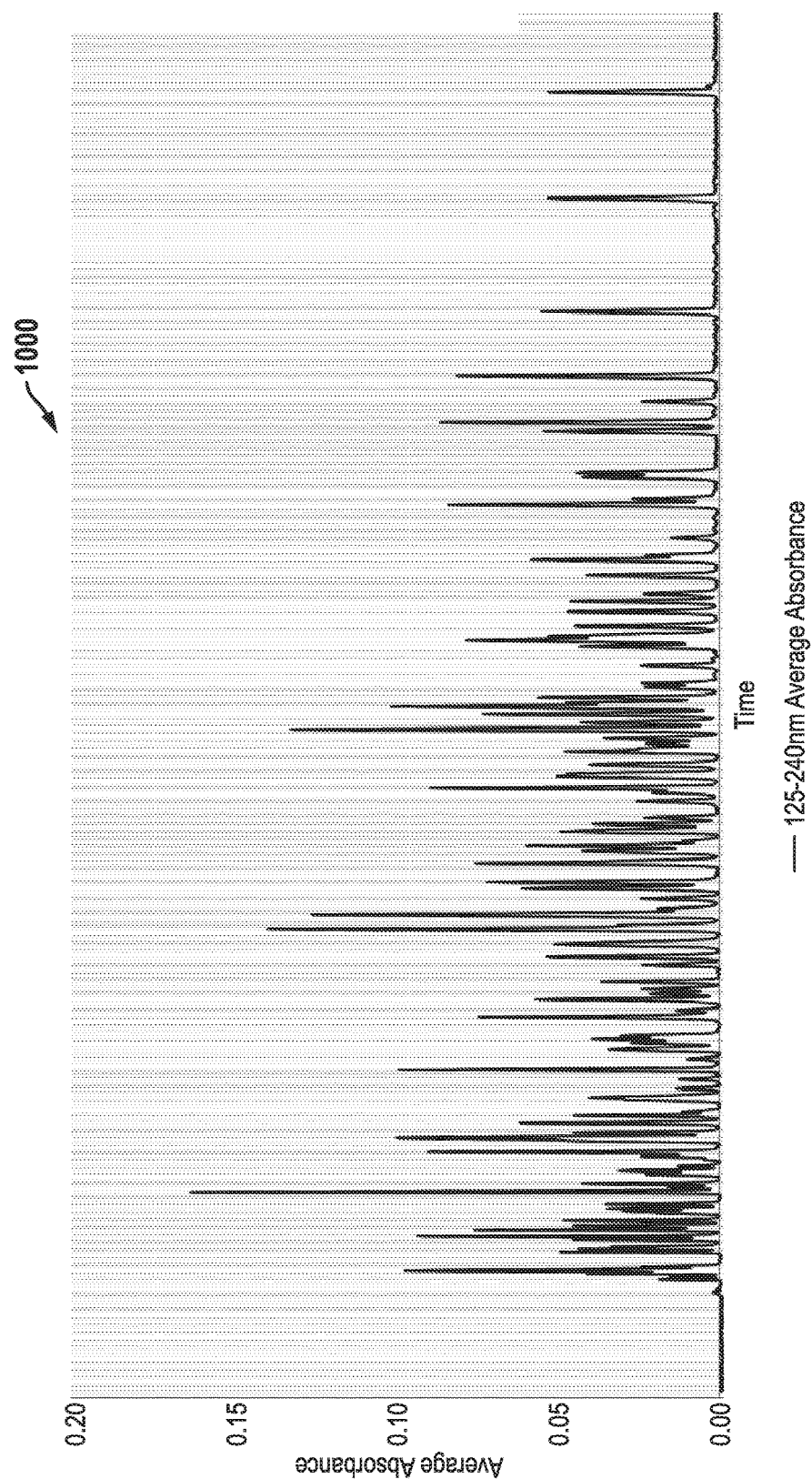
FIGS. 10, 11a and 11b illustrate examples of the classification analysis techniques applied to unleaded gasoline.

An example of the classification approach applied to unleaded gasoline is shown in FIGS. 10 and 11. FIG. 10 shows 125-240 nm average absorbance versus time chromatographic separation 1000 of a 139-component PIONA standard sample. The sample consists of a mix of several representative compounds from each of the five PIONA classes, each at relative weights of about 20%. Included are 11 paraffins, 35 isoparaffins, 25 olefins, 30 naphthenes, and 38 aromatics. The separation was done using a 30 m nonpolar dimethyl polysiloxane phase analytical column, the injector temperature was set to 300° C., the injection volume was 0.1 uL, and the split ratio was 40:1. The carrier gas flow rate was set to 2.3 mL/min. During the separation, the oven was programmed to start at 35° C., and after an initial hold time of 2 minutes, increased at a rate of 10° C./minute with a final temperature of 200° C. The total run time under these conditions is 18.5 minutes. Under DHA conditions, using a 100 m analytical column and a very slow 1° C./minute or 2° C./minute oven ramp rate (depending on temperature), these analytes can be fully separated. However, under the run conditions used in FIG. 10, many instances of coelution occur.

Figure 11A:
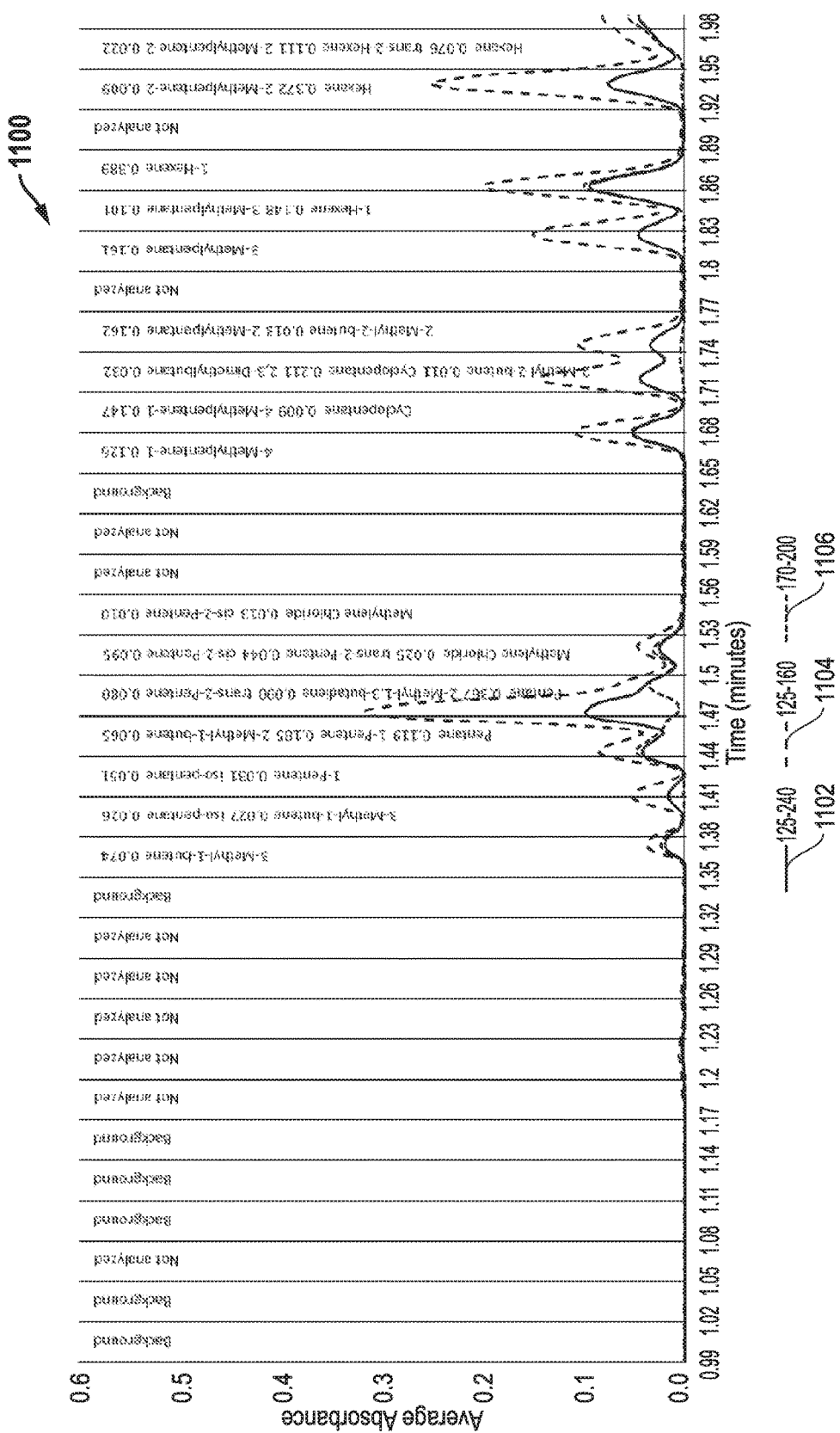
Figure 11B:
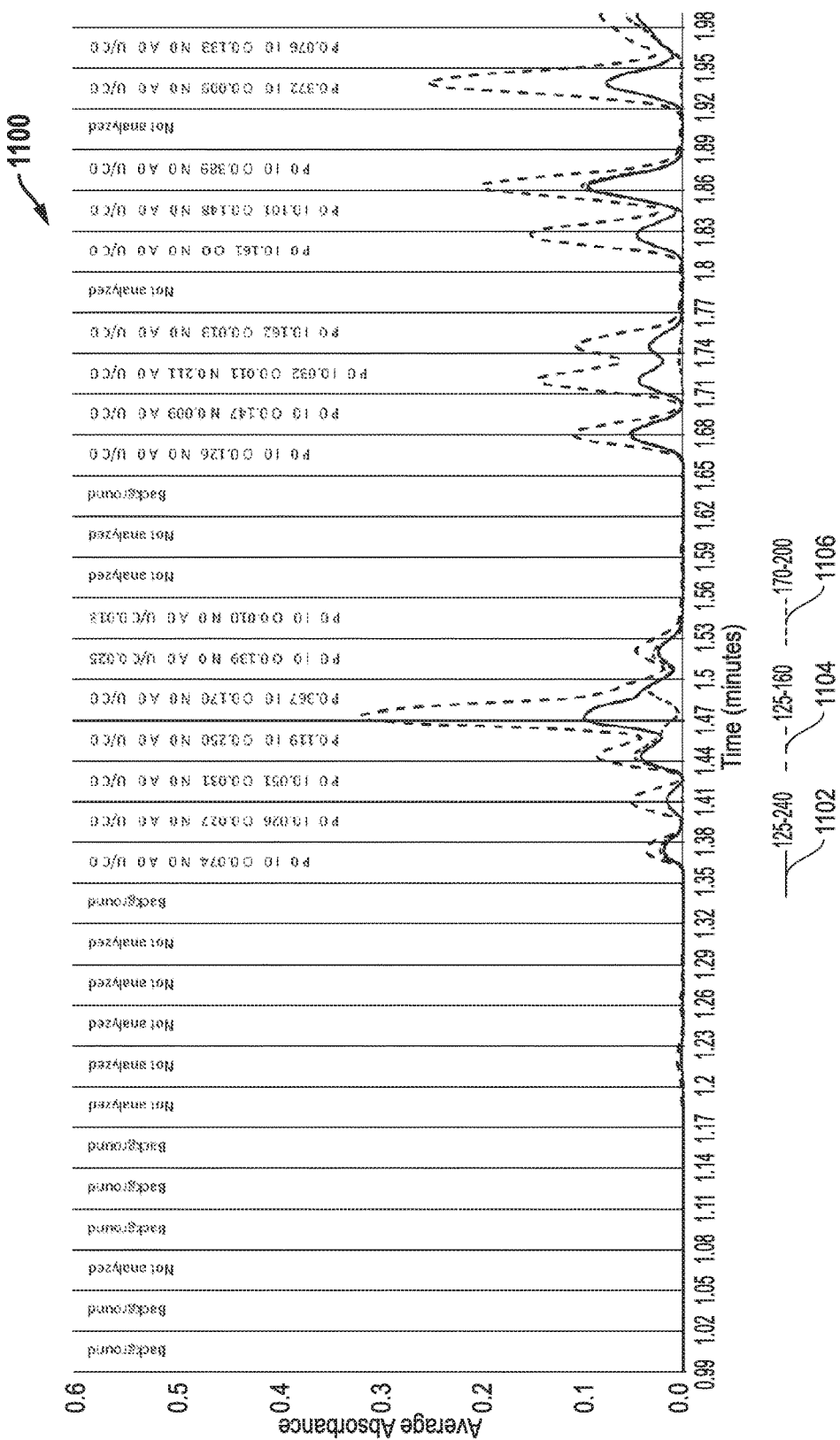

FIGS. 11a and 11b show the average absorbance versus time chromatogram 1100 for 125-240 nm response 1102, 125-160 nm response 1104 and 170-200 nm response 1104.

The chromatogram 1100 is superimposed with the time slices used for the classification analysis described above. A +/40 RI window and a 0.03 minute time slice were used. The detector scan rate was set to about 4.6 scans/second, so a typical time slice contained 8 or 9 scans. The maximum number of possible coelutions was set to three. The quality of the fits were good, which is an indication that this limit was indeed achieved by the experimental conditions. FIG. 11*a* shows the output of the classification algorithm during the first minute where analytes elute. The result of the tiered search at each time slice was the number of coeluting analytes, their most probable identities, and the value of the contribution from each analyte to the total response in the time slice. The algorithm was set to reproduce the full range 125-240 nm chromatogram response, although the reference spectra could have been integrated using one of the other filters, resulting in a reproduction of the corresponding chromatogram response instead.

For each time slice, the class of each analyte was retrieved from the VUV reference library, and the analyte's response added to the total response for that class. The result at the end of the analysis is the total response area for each of the five PIONA classes. These are combined with the class-based relative response factors to convert the areas to relative mass percentage.

A particularly useful way to present the results is shown in FIG. 11*b*, where the class information has been retained. In FIG. 11*b*, the analytes response areas have been added to P (paraffins), I (isoparaffins), O (olefins), N (naphthenes), or A (aromatics) according to their classification. An additional category, U/C has been included to bucket analytes that don't fall into one of the PIONA classes. Note that if multiple analytes belonging to the same hydrocarbon class elute in the same time slice, their responses are each added to the total response for that class, so each of the hydrocarbon class results represents the sum of all analytes of that class that eluted within the time slice.

All of the compounds in the 139-component PIONA standard have reference spectra representations in the VUV reference library, but many of the compounds that occur in a more complicated sample, such as unleaded gasoline, are not. These compounds are represented by the closest reference spectra in the library that also elute within the +/−40 RI window. Due to the class-specific characteristics of hydrocarbon absorbance spectra, the most likely match to an uncharacterized compound is one from the same hydrocarbon class. Therefore, many analytes in a fuel analysis may actually be represented by another analyte's reference spectrum, making the specific identity information meaningless. In addition, it is possible to rapidly build up a reference library consisting of spectra from unidentified compounds, but whose classes are known. This is most easily done using samples from gasoline production streams as previously described. Such reference spectra are very useful for classification analysis but not for specific species identification. In light of all of this, classification results as presented in FIG. 11*b* may be the most meaningful representation of the analysis.

Specific compounds that have well-characterized reference spectra can be singled out, and their area responses applied to a separate bin. In this way, relative weights of specific analytes can be determined if desired, along with bulk classification results. Care has to be taken when combining this notion with cross-analyte characterization just described, although this aspect of the present disclosure is more applicable to higher boiling regions of a fuel analysis chromatogram when the sheer number of molecular compounds make it unlikely that all of them will be characterized. Specific compounds of interest tend to be oxygenates, like methanol, ethanol, and methyl tert-butyl ether, all of which are sufficiently distinct from the PIONA hydrocarbons and also have boiling points low enough that nearly all of the eluting components have representative spectra in the reference library. Another common specific analysis is of the BTEX aromatic complex consisting of benzene, toluene, ethylbenzene, and xylene. Benzene and toluene are the only aromatic compounds that elute in their respective vicinities, and all aromatic compounds up to ethylbenzene and the xylenes are typically specifically characterized. Therefore, specific compounds of interest are generally able to be isolated from the classification results, and a PIONA-type analysis can include relative amounts of oxygenates and several important aromatics.

The result of the classification analysis are the total response areas for each of the classes and each of the individual analytes of interest. Equation 4 is used to convert the areas to relative mass, but now the subscripts a and i in eq. 4 can refer to individual analytes or classes of analytes. The denominator of eq. 4 still has to have a term for each specific analyte or analyte class binned during the classification analysis. However, there is no requirement to include a term for every specific analyte. The contributions from most analytes in a classification analysis will typically be included in one of the class results.

To include results for a particular analyte, for example benzene, along with a PIONA analysis, the total area response for each of paraffins, isoparaffins, olefins, naphthenes, and aromatics is multiplied by the corresponding class-specific RRF. The total area response for benzene is multiplied by its RRF, which could be taken from its library value, or alternately the aromatics class RRF can be used. The area response for aromatics does not include the contribution from benzene, which is now being handled separately. When forming the denominator in eq. 4, the products formed for the five PIONA classes and benzene are included in the sum. To find the mass % for each of the five classes and benzene, each individual product is divided by the denominator and the result multiplied by 100. When reporting the final class-based results, the mass % for benzene is added to the mass % result for aromatics to determine the total aromatics content, if desired. The result for a compound not belonging to one of the PIONA classes is treated similarly, but its result is not added to any of the total class results for reporting purposes. An additional "unknown" or "other" class can be included to account for compounds not belonging to any class of interest.

For the analysis of the 139 component PIONA standard, the RRFs for paraffins were calculated relative to the methane cross section via Eq. 7. A paraffin class RRF was calculated from the average of the C5-C13 RRFs. The known relative mass % for the five PIONA classes in the 139 component standard was used along with the paraffins RRF to calibrate RRFs for the other four PIONA classes. Other molecule-specific RRFs were generally calculated from eq. 7, although some are assumed equal to the corresponding class-based RRF, if available. The class-based RRFs used for the PIONA classification analysis are given in Table 1.

TABLE 1

Class-based relative response factors used for analysis of 139 component PIONA standard.

| Hydrocarbon Class | Relative Response Factor |
| --- | --- |
| Paraffin | 0.769 |
| Isoparaffin | 0.781 |
| Olefin | 0.541 |
| Naphthene | 0.773 |
| Aromatic | 0.296 |

Figure 12:
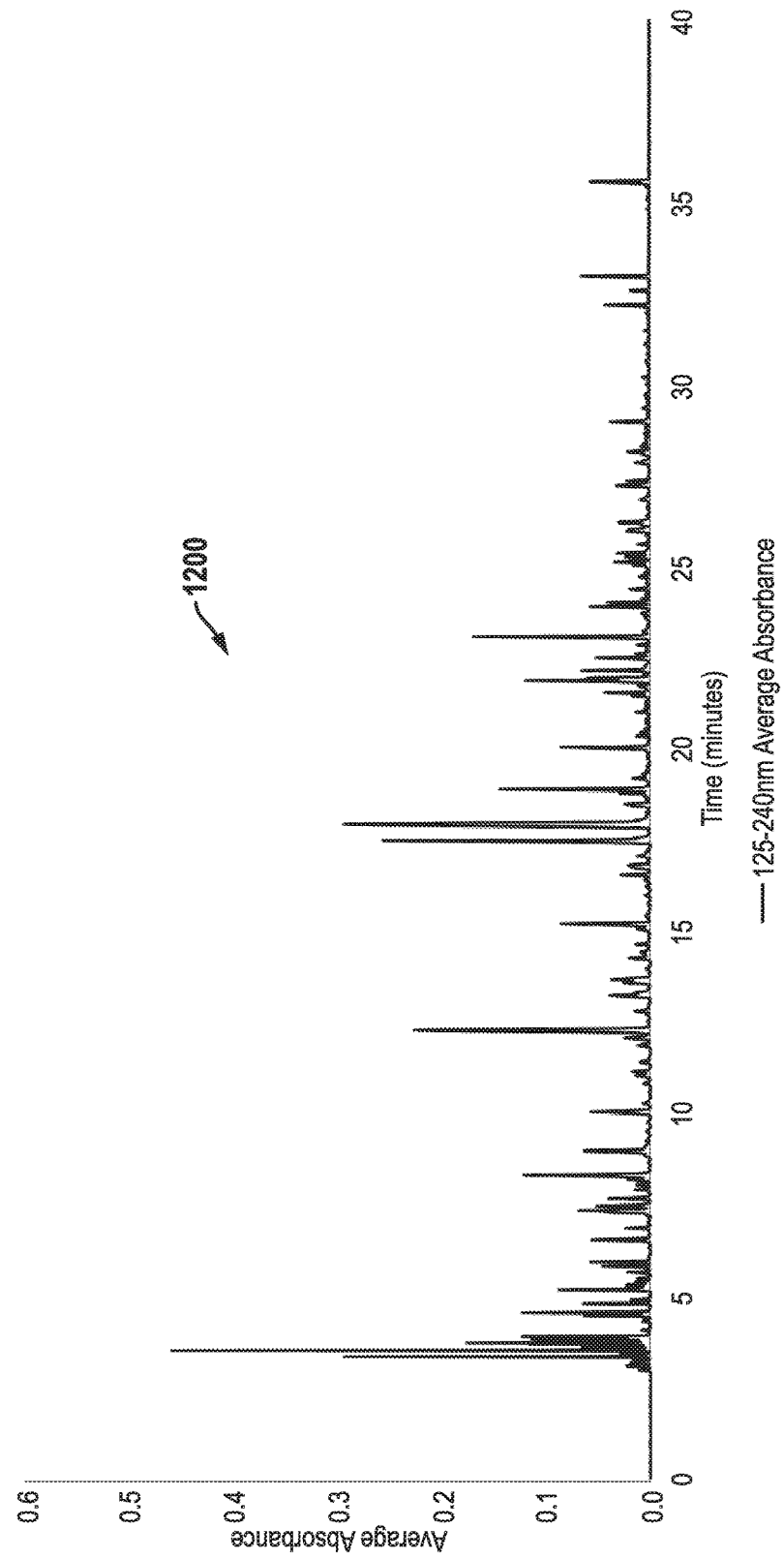
FIG. 12 illustrates a chromatogram of a PIONA VI standard.

A further example of the classification method applied to a PIONA VI standard is illustrated in FIGS. 12 and 13. A PIONA VI standard sample is representative of unleaded gasoline. Gasoline contains of all of the compounds that occur in the 139 component PIONA standard, but also many other compounds that don't. However, most of those additional compounds fall under the same five PIONA classes. FIG. 12 shows a 125-240 nm average absorbance versus time chromatogram 1200. The chromatogram 1200 is from a 0.3 uL injection of PIONA VI standard at a 50:1 split ratio. The injector temperature was held at 300° C. The carrier gas flow rate was set to 0.7 mL/min. The oven temperature started at 30° C. and was held there for 10 minutes, then increased at a rate of 5° C./minute until it reached 200° C. The total run time was 44 minutes, although all compounds had eluted by ~37 minutes.

A preliminary analysis showed that the 139 components from the PIONA standard is a good starting set of reference spectra, but not sufficient to fully characterize the PIONA VI standard. Many additional reference spectra were added to the VUV reference library from a variety of sources, including samples from gasoline production streams. A DHA-type separation was performed on the PIONA VI standard, using a 100 m DHA column and slow temperature ramp. A handful of compounds were identified and added to the VUV reference library from this data.

Importantly, the PIONA class-based relative response factors were not modified for the PIONA VI analysis, and are the same ones that were used for the 139 component PIONA standard. Table 2 shows a comparison between class mass % values available from the PIONA VI certification documentation and the GC-VUV classification analysis. The GC-VUV results are averages of three runs. The correlation between GC-VUV classification measurements and the PIONA VI certification information is very strong. Note that the relative amounts of each of the classes is quite different from the 139 component standard with which the GC-VUV RRF values were calibrated. Clearly, the GC-VUV measurement is responding correctly to these variations in relative mass %. The advantage of the current disclosure is that the GC-VUV measurement was done using a 30 m column under conditions where all analytes had eluted before 40 minutes. These conditions are much simpler to implement and the measurement times much shorter than the methods described in ASTM D6730 and ASTM D6839, which represent the current state of the art.

FIGS. 13a-13f show a graphical representation of the mass % results shown in Table 2 as well as a carbon-number breakdown of the results.

TABLE 2

Comparison of PIONA VI certification and GC-VUV measurements of PIONA mass %.

| | Mass % PIONA VI Certification | Mass % VUV (Average) |
| --- | --- | --- |
| Paraffins | 16.92 | 16.57 |
| Isoparaffins | 33.02 | 34.17 |
| Olefins | 7.56 | 7.86 |
| Naphthenes | 11.3 | 10.86 |
| Aromatics | 20.96 | 22.03 |

Figure 13A:
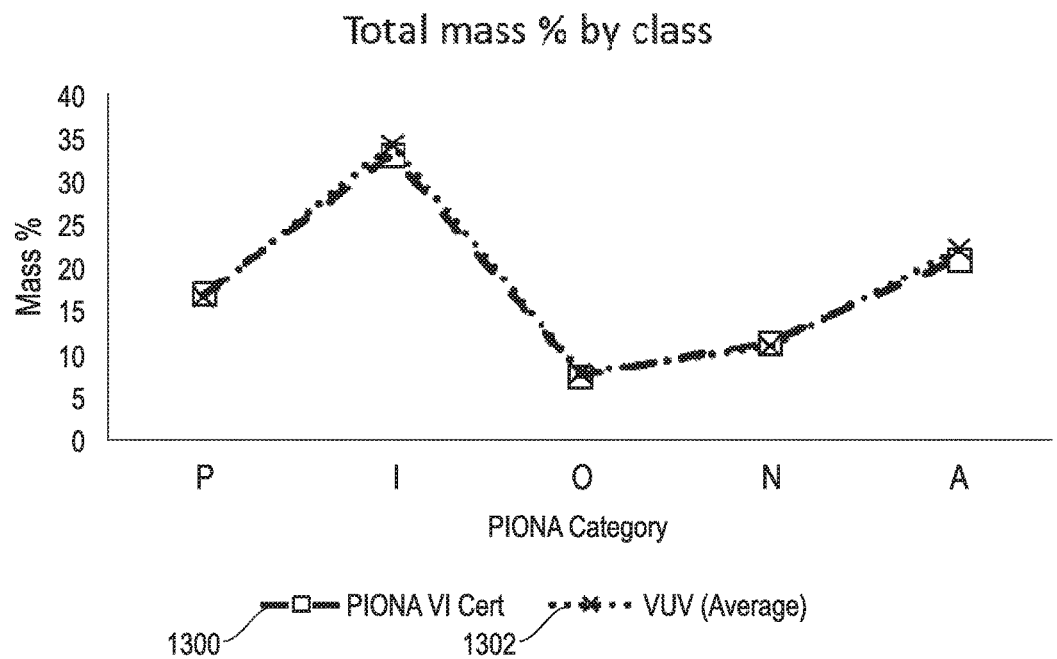
FIGS. 13a-13f illustrate graphical representations of the mass % results shown in Table 2 as well as a carbon-number breakdown of the results.
Figure 13B:
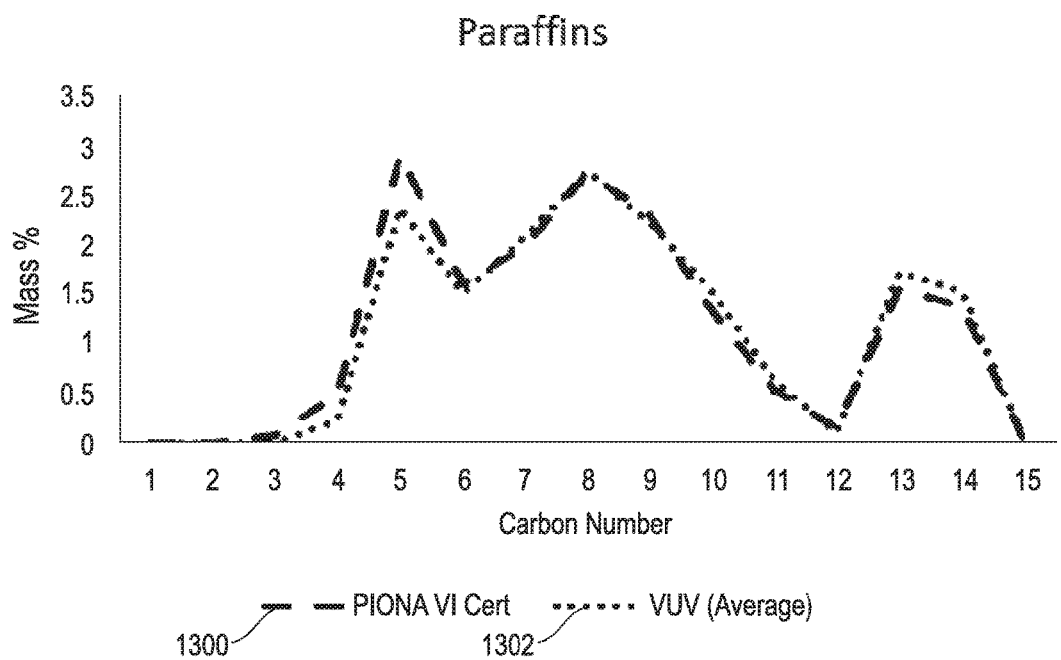
Figure 13C:
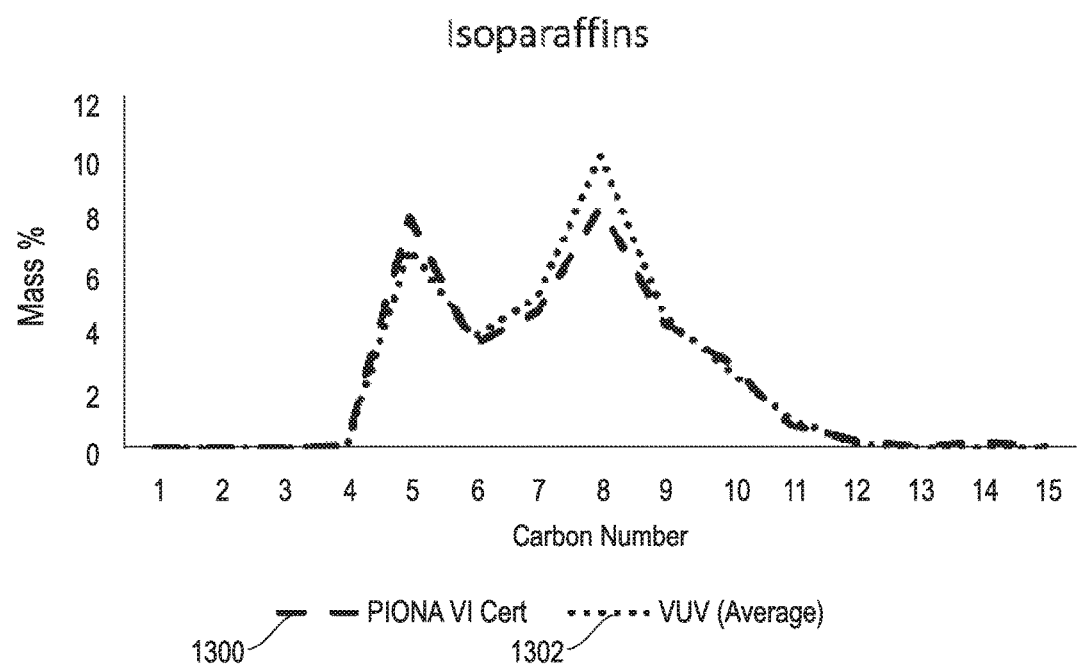
Figure 13D:
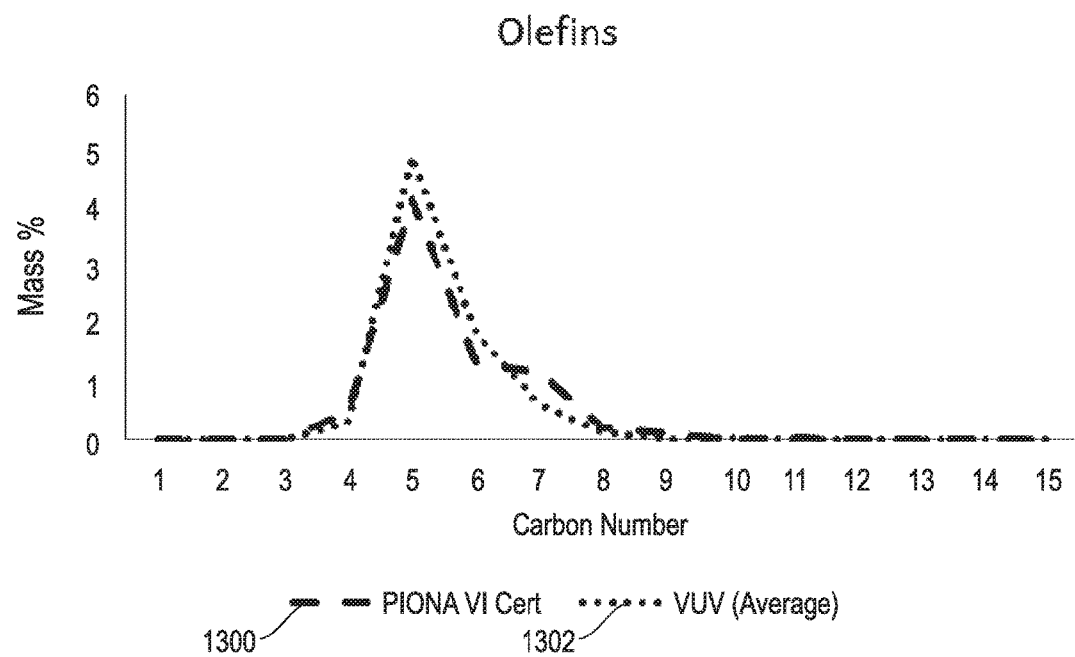
Figure 13E:
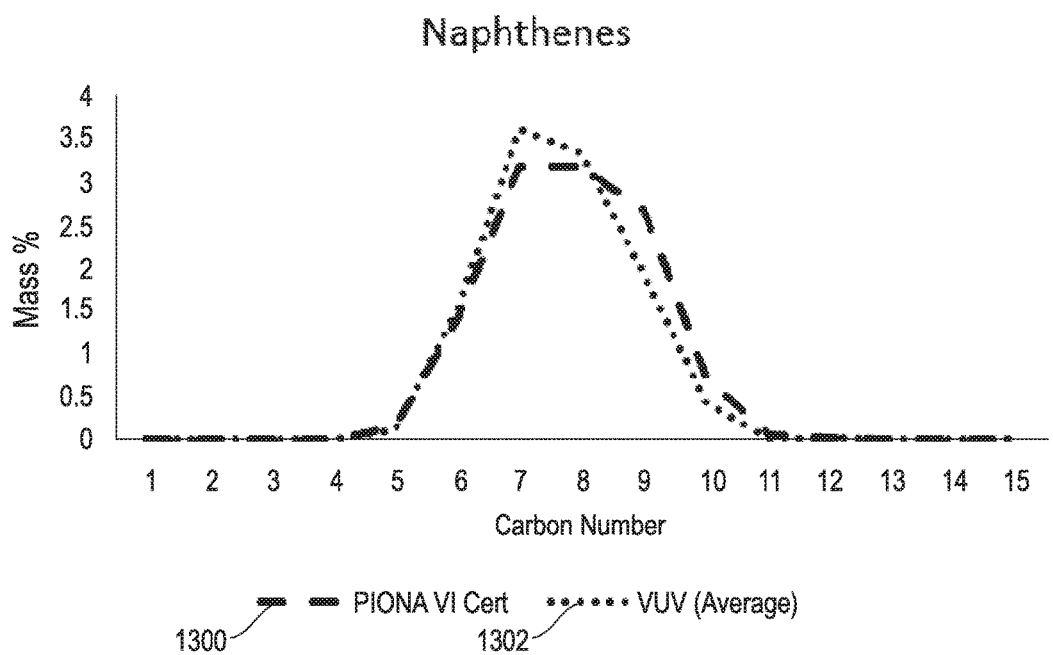
Figure 13F:
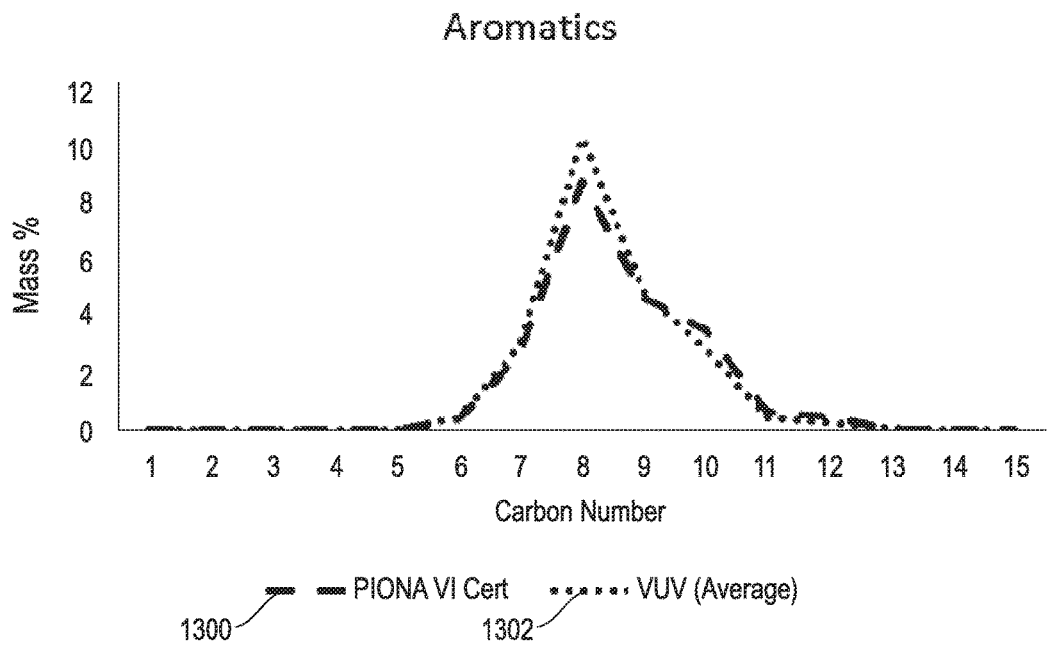

FIG. 13a shows a total mass % by class by plotting mass % versus the PIONA category. FIGS. 13b-13f graphically represent mass % versus carbon number for paraffins (FIG. 13b), isoparaffins (FIG. 13c), olefins (FIG. 13d), naphthenes (FIG. 13e) and aromatics (FIG. 13f). For each of FIGS. 13a-13f graphs 1300 for the PIONA VI certification and graphs 1302 for the VUV (average) results are provided. Elution times using standard boiling-point type chromatography are highly correlated with carbon number for a given hydrocarbon class. Therefore, it is relatively straight-forward to associate a carbon number with retention time for a given chromatographic run. In cases where a molecule has a specific representation in the VUV reference library, the carbon number is simply taken from the molecule's chemical formula. Where a molecule's identity is not known, but its class is, a carbon number is associated with its entry in the VUV library, where the carbon number is estimated by the molecule's retention index and hydrocarbon class. When an analyte occurs in the classification analysis, its response is added to a running tally for the analyte's class and carbon number.

In FIGS. 13a-13f, the GC-VUV measurements are again averages over three runs. The agreement between the PIONA VI certification and the GC-VUV measurements is quite good. Differences on this level can be helpful in improving the GC-VUV PIONA measurement, since it points to specific regions where class-based reference spectra in the VUV reference library can be added or improved. In addition, the RRFs can be refined, and class-based RRFs could be further broken down into groupings by carbon number. However, it should also be noted that the PIONA VI certification values themselves were obtained via DHA measurement, and no attempt has been made to account for the variation inherent in such measurements, which can be substantial. In addition, the DHA method is less accurate when measuring certain classes at specific boiling point ranges, for example naphthenes and aromatics at higher carbon numbers (ASTM method D6730). Therefore, care must be taken in comparing these results, and absolute correctness of the PIONA VI certification results should not be automatically assumed.

In either of the detailed or classification approaches, a method for automatically locating and updating retention times for a list of analytes is beneficial. In one embodiment, the list of analytes is the list of retention time markers used with the classification approach. Since the retention order for all other analytes are estimated via retention indices and interpolation between the retention time markers, automatically updating the retention times for the retention time markers for each sample run makes the determination of elution order more accurate. This amounts to determining the $t_i$ in eq. 8 each time a new measurement is done.

The list of analytes used as retention time markers will typically have accurate reference characterizations in the VUV reference library. The analytes will also have highly characteristic spectra, making them hard to confuse with other molecules. For example, aromatics like benzene, toluene, and xylene make good candidates, as to PAHs such as naphthalene and methylnaphthalene. Linear alkanes tend to stand out due to their particular spectral characteristics compared to other hydrocarbon classes. However, the linear alkanes tend to be harder to distinguish from each other at higher carbon numbers, so some use of retention time information is helpful when automatically searching them from a chromatogram.

A method for automatically locating the elution time of an analyte in a GC-VUV experiment is now described. In the following, the specific analyte being searched for is referred to as the "search analyte". The first step is to divide the chromatogram into time slices. The time slices can be the same ones used for the corresponding classification analysis, but don't have to be. The time slices can also be the analysis windows of the detailed approach. The time slices don't have to be of the same width or even be contiguous. A rough retention index scheme can be used to narrow the amount of chromatogram to be searched, and the library of candidate analytes reduced using retention indices or other constraints. Finally, literal time slices don't have to be used at all, and the fit procedure can simply be done on each of the measured absorbance scans.

Figure 14:
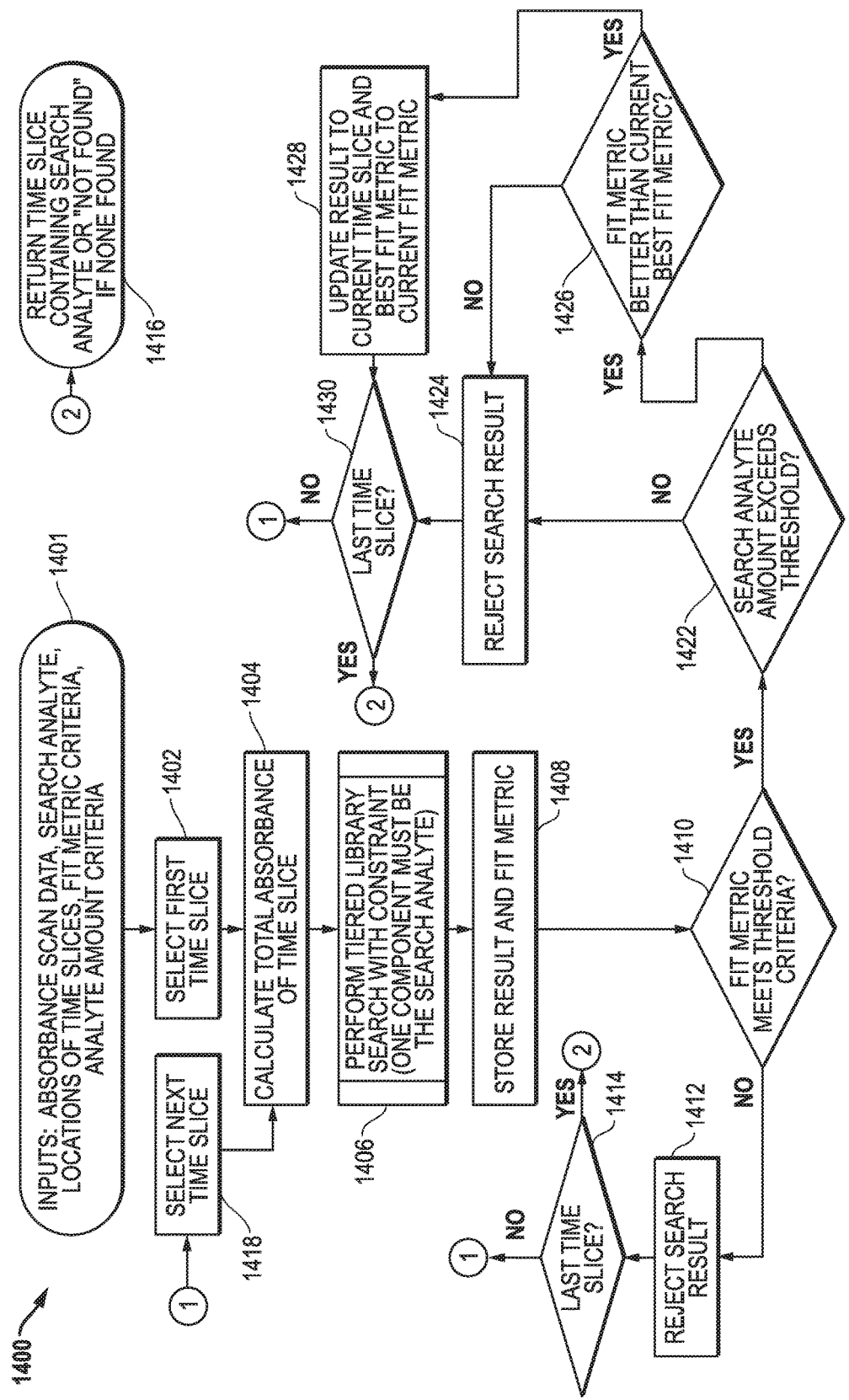
FIG. 14 illustrates a work flow for automatically locating the elution time of an analyte in a GC-VUV experiment.

One embodiment is illustrated by a flow diagram 1400 in FIG. 14. The inputs for the flow diagram are shown at step 1401 ("Inputs: Absorbance scan data, search analyte, locations of time slices, fit metric criteria, analyte amount criteria"). Thus, the inputs to the routine include a chromatographic set of data consisting of times and absorbance scans, a list of times representing the time slices, the identity of the search analyte, a list of candidate analytes to use in a tiered search, an overall fit metric criteria, and a criteria on the relative amount of search analyte. At step 1402 a first time slice is selected. Next the flow moves to step 1404: "Calculate total absorbance of time slice." At each time slice, the total absorbance of the time slice is constructed from a wavelength-by-wavelength summation of all absorbance scans in the time slice, just as with the classification approach. A list of candidate analytes can be pre-generated through use of retention indices or other constraints, but this isn't strictly necessary. At step 1406 ("Perform tiered library search with constraint (one component must be the search analyte") a tiered search is performed, but a model used at each stage is constrained to have one component equal to the search analyte. This removes one order of complexity at each step of the tiered search process. For the single-analyte stage, only one candidate is considered, namely the search analyte. The result of this single fit is stored, along with the fit metric (again, $\chi^2$, $R^2$, or other). In the second stage, a two-component model is assumed, but one component is required to be the search analyte. The result is that only n fits need to be done for a list of n candidate molecules, even though a two-component model is assumed. The results of this search are ranked according to best fit metric, and the best fit compared to the single component search. If the fit metric is significantly improved over the single component case, then the result is updated with the best two component result. If not, then the best single candidate result is retained. The third stage considers a model consisting of three components, but again one is constrained to be the search analyte. A total of $$\frac{n!}{2(n-2)!}$$

regression fits are done for a list of n candidate analytes. Again, the best fit from the third stage must be significantly better than the results from prior stages in order to consider updating the result. Again the procedure can be carried forward through 4- and 5-component searches if desired, although a particularly advantageous embodiment limits the search to a maximum of three total components.

The result is the simplest model that explains the measured absorbance of the slice and also contains the search analyte. At step 1408 the result and fit metric are stored. The results may then be evaluated at step 1410 ("Fit metric meets threshold criteria"). Here, some additional care is required in evaluating the results. An overall fit metric threshold is useful since most of the fits will not be very good. After all, most regions of the chromatogram will not contain the search analyte. Nevertheless, it is still possible to achieve a good fit even when the search analyte is not present. For example, if only one analyte elutes in a time slice the second stage of the tiered search can yield a good fit where the fit weight for the search analyte is essentially zero. Consequently, it is desirable to include a criteria on the relative amount of the search analyte present as well as the quality of the fit.

The flow diagram in FIG. 14 illustrates a particular order in the implementation of the fit criteria, namely, a fit metric threshold is checked first at step 1410, and if the search passes this, an amount or relative amount threshold on the search analyte is checked at step 1422 ("search analyte amount exceeds threshold"). If the check at step 1410 is negative, the search result is rejected at step 1412. At step 1414 it is determined if the time slice is the last time slice. If not control passes to step 1418 ("select next time slice") and then again to step 1404. If the check at step 1414 is affirmative, then control moves to step 1416: "Return time slice containing search analyte or 'not found' if none found."

Candidate results should meet both criteria of steps 1410 (fit metric) and 1422 (analyte amount) and are then further ranked according to best fit metric. If the check at step 1422 is affirmative, control passes to step 1426: "Fit metric better than current best fit metric?" As shown in the flow diagram, if the search at a particular time slice passes the fit criteria, and further the fit metric for the current slice is better than the currently stored "best fit", control moves from step 1426 to step 1428 ("update result to current time slice and best fit metric to current fit metric") where the result is updated to the current slice and the best fit metric value updated to the value of the current fit metric. From step 1428 control moves to step 1430 where it is determined if the time slice is the last time slice. If the time slice is the last time slice, control moves to step 1416 and if the time slice is not the last time slice control moves to step 1418.

If the check at step 1422 is negative, then control moves to step 1424 where the search result is rejected and then to step 1430.

Likewise, if the check at step 1426 is negative, then control moves to step 1424 where the search result is rejected and then to step 1430.

Clearly, multiple variations on the implementation of the search criteria are possible. For example, the amount criteria can be verified first, after which the search results are ranked according to best fit metric. As another example, the final ranking can be done by search analyte amount instead of best fit metric.

For the purpose of ranking fit results from different time slices, the $R^2$ fit metric has particular advantages over the $\chi^2$ fit metric. Since the $R^2$ includes a dependence on the magnitude of the measured absorbance, a good $R^2$ value implies both a good fit to the data and a significant measured absorbance. By contrast, a very low absorbance magnitude tends to result in a good $\chi^2$ values, and minor systematic errors in measured absorbance spectra can cause higher $\chi^2$ values even when the fit is better. In short, the $\chi^2$ statistic may be suitable for comparing the outcomes of different model fits to the same measured absorbance spectrum, but is not particularly well-suited to comparing the quality of model fits to different measured absorbance spectra. Therefore, one combination of metrics to rank the results from multiple time slices is to rank by best $R^2$ and most relative amount of search analyte. An example of the corresponding fit criteria might be to require $R^2$ values better than 0.98 and more than 50% relative mount of retention time marker. If multiple time slices meet the criteria, the slice yielding the best $R^2$ value is chosen.

The above analyte search can be combined with the classification approach and used to automatically update retention times of retention time markers. When a method is set up, a list of retention time markers is constructed with their approximate elution times and retention indices. On a subsequent run of the same method, each retention time marker can be searched in the chromatogram, and the elution time updated according to the result of the search. The same time slices that are to be used for the classification analysis can be used, and the retention time can be set to the midpoint of the slice where the best match for the retention time marker was found. This procedure is carried out for each retention time marker in the list. In each case, since an approximate elution time is already known, the search for each analyte only needs to be done over a few time slices in the vicinity of the stored elution time. On the other hand, if all time slices are searched during this stage, the total absorbances of the time slices can be reused during the subsequent classification analysis. Either way, the result of the retention marker search is an updated list of elution times for all of the retention time markers relevant to the current chromatogram, and a correspondingly more accurate determination of retention indices for the rest of the chromatogram. If retention indices for the reference analytes have been accurately determined, for example by calculating them using the method itself, then the size of the RI window used in the classification approach can be reduced. This may result in a more accurate analysis, but regardless will result in a faster analysis. If one or more searches does not yield a satisfactory result, that retention time marker can be dropped from the list for that analysis. If enough retention time markers are used, dropping a few of them will not significantly impact the RI determination. If too many retention time markers have been dropped, then the analysis can be halted, or the analysis can revert back to the original retention time marker list and use the times stored during method setup.

Due to the constraint that one of the components in the tiered search is known, it is practical to use fewer constraints and thus larger subsets of the VUV reference library to search the retention time markers. In one embodiment, retention indices may not be used at all for this purpose. In another embodiment, very rough estimates of retention indices may be calculated by using the start and end times of the run. The retention time marker searches are then performed using larger retention index windows. The automated retention time marker search can even replace the need for a predefined list of retention time markers and times. When using a non-polar phase analytical column, simply providing a list of marker analytes may be enough. Each marker is located without using elution time or RI constraints, or possibly using rough estimates of their elution times. The retention marker list consisting of known RIs and determined elution times is built up automatically as each marker is found.

In another embodiment when used with the detailed approach, the elution time of the retention time markers is stored along with the analysis method, which also includes the locations and analyte models for all of the analysis windows. On a subsequent method run, any shift in the elution times of the retention time markers is used to correct the locations of the analysis windows accordingly, for example by interpolating between the closest markers that elute before and after the analysis window. Since the locations of the retention time markers are already approximately known, the search for each retention time marker only needs to be done over the analysis window/windows where that analyte occurs and surrounding regions.

A further embodiment combines the detailed approach with the tiered search, first described in conjunction with the classification approach. During the setup of a detailed method, analysis windows are set up manually or automatically using a peak integration routine. A tiered search can be performed on each of the analysis windows in order to determine the model structure associated with the analysis window. Basically, the result of the tiered search for the analysis window is the model structure, since the tiered search identifies the analytes whose reference spectra are to be used in eq. 3. In this case, the inputs to the tiered search are the total absorbance corresponding to the analysis window and a list of candidate reference analytes. The list can consist of the entire VUV reference library, but more advantageously is a constrained list reducing the number of reference analytes that are to be considered. The list can be constrained by use of retention times/indices, molecule/ compound class, molecular formula, type of sample, etc. When used this way, the tiered search only needs to be done once for each analysis window as the method is built. On subsequent runs, the model structure pre-determined for each window may be used to perform the deconvolution. Alternately, the entire procedure, including tiered search, can be performed each time a sample is measured.

A further embodiment combines the classification approach with deconvolution to create a new type of peak integration routine. After the tiered search is completed for each time slice, a model equation consistent with the results of the tiered search is used to fit each individual absorbance scan in the time slice (Eq. 3 using reference spectra of the compounds identified by the tiered search). The result is a deconvolution of the response for the time slice into contributions from each of the analytes that eluted within the time slice. This can used as a way to visualize the results for a time slice. After a classification analysis, a user can select a particular time slice to view the deconvolution results, which can be presented in a popup window. The deconvolution could be done for all of the time slices, in which case the classification analysis also functions as an automatic peak integration routine. The areas of the individual components have already been determined during the tiered search phase of each time slice analysis. The deconvoluted result can be used as further verification of the classification analysis. For example, the continuity of deconvoluted responses at slice edges can be verified.

In a further embodiment of the classification approach, a method for automatically subtracting a background spectrum is provided. A threshold condition is provided that must be exceeded in order for a time slice to be analyzed. If the threshold condition is not met, the analysis of the time slice is skipped and the next time slice considered. In a case where a time slice analysis is skipped, the time slice is considered as a candidate for background representation. A second threshold condition is checked, and if the absorbance properties of the time slice meet the threshold, a background absorbance scan is constructed from the average absorbance of the time slice. This background absorbance spectrum is subtracted from all subsequent absorbance scans until another time slice meets the background threshold condition. The threshold condition can be a condition on the amount of change in absorbance across a time slice, either by considering the measured absorbance scans or the integration filter responses. The threshold conditions for analyzing a time slice and updating a background can be the same, or two distinct thresholds can be provided.

An option to use a background file can be provided. Periodically, a GC-VUV run can be done using the same conditions as the GC-VUV sample analysis. However, in this case no injection is done. The chromatographic data consisting of absorbance scans and chromatogram response can be used as a background reference for subsequent GC-VUV runs of actual samples. In this case, the GC-VUV method stores the location of the background run, and absorbance scans from the background file are subtracted from absorbance scans of the sample runs. The background scans will ideally come from the same time regions of the chromatogram as the absorbances from which they are subtracted. This background subtraction methodology can be combined with either the detailed or classification approach.

An option to explicitly define a background region can be provided. Multiple background regions can be defined and the background absorbance updated from the absorbance scans in these regions. Absorbance spectra collected at subsequent time regions have one of the background scans subtracted out before being used in analysis. The background scan used can be the most recent one prior to the absorbance scan, or can simply be the closest one if doing analysis offline.

In the detailed approach, each analysis window can have a background spectrum associated with it. Each analysis window can alternately have a time region defined from which it extracts a background scan. The background scan can be extracted from the same chromatogram containing the analysis window, and can be updated for each analysis.

It is possible that an absorbance scan can saturate for high values of absorbance. "Saturation" in this context means the transmittance is essentially zero, causing the absorbance to be essentially infinite. In an actual spectroscopic experiment, this condition manifests as a particularly noisy and unphysical scan result at absorbance values above a particular threshold. Due to highly wavelength-dependent nature of absorption cross sections, it is common that only part of the absorbance saturates when this occurs. One way to deal with this is to simply cut those absorbance values out of a fit. An absorbance saturation threshold can be set, and wavelength where absorbance values exceed the threshold are dropped from the analysis. This can be handled automatically by the analysis software and can be implemented in either the detailed or classification approach. When this is done, a chromatogram response is reconstructed that contains the saturated region, the reconstructed response is actually a prediction of what the measured chromatogram response would have been had the saturation not occurred. This is accurate as long as the fit results are accurate. This fact can be used advantageously in cases where a sample consists of constituents having a wide range of concentrations. More sample can be put on-column by increasing the injection volume or reducing the split ratio in order to enhance the signal from lower concentration constituents, even if doing so causes the absorbance signal from some of the higher concentration constituents to be large enough to saturate in some wavelength regions. In this way, the dynamic range of concentrations that can be quantified for a given sample is increased.

In one embodiment, the time slices used in the classification approach are determined by the aforementioned peak detection/integration routine. Such peak integration routines are known in the art and provide a means for determining peak locations and areas using standard two-dimensional chromatogram responses. A split/overlapping peak is typically divided into two peaks at a valley point between them. Peak shoulders or peaks on the tails of other peaks are also typically sectioned off using some approximation technique. As such, the peak detection part of peak integration routines estimates time regions of specific peak events, where the regions involving split peaks and/or shoulders are divided into multiple, but connected, sections. Further, each region with significant response will typically be included as part of one of the detected peaks. Thus the time regions determined by application of a standard peak detection/integration algorithm are suitable to use as the time slices in the classification routine, which does not require equal or even contiguous time slices. Note that the peak areas determined by peak detection/integration routines are not accurate in cases of split/overlapping peaks or shoulders because they do not correctly take into account the individual compounds' contributions to the response. In addition, a peak integration routine does not deal with perfect or near-perfect coeultion, and tends to identify such cases as a single peak.

A peak integration routine is used to determine distinct peaks from one or more GC-VUV chromatogram filters. The time regions associated with detected peaks become the time slices used in the classification algorithm. In this case, the term "elution event" is more appropriate than "peak" since one embodiment involves simple, fast separations having many coelution events. These coelutions are advantageously resolved during the tiered search step of the classification method, and the peak areas for each of the coeluting analytes are determined, as was already described. Thus, coelution events leading to split/overlapping peaks, shoulders, tailing, or perfect coelution are correctly treated.

The classification approach does not necessarily represent every compound that may occur with a specific characterization. However, if such a representation is provided, detailed information about the compounds is provided by the classification approach, as was already described. A specific representation for all compounds involved can be provided, in which case the classification approach provides detailed information about all of the compounds in the sample, in particular the peak area that results for each distinct component in the sample. These peak areas are used to determine the concentration of each component, for example its relative mass %, volume %, or mole %, in the original sample, as has already been described. In this case, bulk quantities can be determined by binning class-based results during the analysis, or by combining the detailed results according to desired classifications at the end of the analysis.

If desired, a GC separation sufficient to resolve all or nearly all elution events may be performed, and in this case a distinct peak occurs for each constituent in the sample. For example, the separation conditions described in ASTM D6730 for detailed hydrocarbon analysis can be used in a GC-VUV experiment to measure a complex fuel sample. To determine the time steps used in the classification approach, the chromatogram is divided into time slices, but having widths smaller than a peak width. Alternately, a peak integration routine is used to determine the time slices from the distinct peak events. A specific representation for each known constituent that may occur in gasoline can be provided in the VUV reference library. In this way, the classification approach provides a detailed hydrocarbon analysis of a fuel sample but with several advantages over ASTM D6730 using GC-FID. The first is significantly reduced possibility of peak misidentification. Retention indices are used to identify a candidate list of analytes, but the tiered search literally finds the correct analyte from that list. With a wider retention index search window, moderate shifts in retention times can be tolerated since the correct analyte is still likely to be in the list of analytes searched. For more severe problems, like a large shift in retention times, the fit metric from the tiered search gives a further means for evaluating the quality of the result, and a problem like this can be flagged. Additionally, like all the other described embodiments, this embodiment can be combined with an automated retention time marker update procedure to make the retention index determination more robust. Setup of the method is much less tedious since control of elution times is less stringent. Tuning experiments for the pre-column are not necessary, and in some cases the pre-column may not be used at all. Finally, correct peak areas are determined even when tailing or coelution is involved.

In cases of more thorough GC separation like this, the classification approach may be further constrained by allowing only two coelutions instead of three or more. If the influence of overlapping peaks is known to be insignificant, then a single analyte at a time may be allowed in the classification approach.

In cases where detailed information on a molecular constituent is desired, but a literal reference spectrum is not available, a reference spectrum from a closely related molecule or compound can be added to the VUV reference library in its place. This reference spectrum will come from another analyte of the same class and possibly of the same carbon number. The substituting reference spectrum may be a linear combination of other such spectra. Regardless, the substituted reference spectrum is added to the library in place of the desired molecule's reference spectrum. All other quantities, such as the molecule's molecular weight and retention index, are associated with the actual molecule of interest.

In some cases, the substituting reference spectrum may be obtained from a compound of a different carbon number. Comparisons of absorbance spectra for different molecules shows that spectra of long chain molecules that differ only in the addition of a carbon at the end of the chain have very similarly shaped absorbances, especially as the chains get longer. Examples include the linear alkanes: for example, the shapes of undecane and dodecane absorbance spectra are quite similar—if a reference spectrum for dodecane were not available, the reference spectrum for undecane may be used to approximate it. In this case the reference spectrum for undecane would occur twice in the VUV reference library, once in the entry for undecane and again for dodecane. Similarly the spectra for 3,3-dimethylheptane and 3,3-dimethyloctane are expected to have similar shapes, and one may approximately substitute for the other.

In general, differences in actual reference spectra can sometimes be used to predict the approximate shapes of reference spectra for other compounds having known structure, but as of yet uncharacterized VUV absorbance. The uncharacterized reference spectra can be approximated by direct substitution of other reference spectra, or by perturbation of other known reference spectra. Rigorous computational chemistry calculations can be used to simulate the shapes of molecular absorbance spectra. The current state of the art in this regard usually does not produce spectra of sufficient quality to use in place of actual reference spectra. However, these calculations can sometimes produce meaningful data on how absorbance spectra differ for certain variations of molecular structure. In other words, rigorous simulations of different molecular structures can reveal how to perturb measured reference spectra in order to create approximations for molecules whose reference spectra are not yet known.

In another embodiment, complex samples are separated using multi-dimensional GC. One type of multidimensional GC makes use of modulation techniques in order to periodically condense effluent from a primary column and introduce the condensed portion to a second column, usually of a different stationary phase than the primary column. This type of GC is often referred to as GC×GC (pronounced "GC by GC"). The modulation can be thermal modulation. In this case, the effluent is rapidly cooled to re-condense the analytes in a modulator region. The modulator region is rapidly reheated and the gas flow redirected to introduce the condensed effluent to the head of the secondary column in a very tight band.

The modulation cycle is typically very fast, on the order of a few seconds. The result is a primary separation driven by the chemistry of the first column and the oven temperature ramp, followed by a secondary separation driven by the chemistry of the secondary column. The detection typically occurs after the secondary separation. The resulting chromatographic signal is usually plotted in three-dimensional form, with the x- and y-axes representing the time axes for each of the columns, and a scalar value (often represented by a color scale) representing the magnitude of the detector response. A second type of modulation uses flow modulation, where a high flow is used to compress the effluent and introduce it to the secondary column. While not explicitly discussed herein, it is noted that both of these multidimensional GC approaches could be further extended to higher dimensions (i.e. GC×GC×GC, etc.) It follows that the analysis benefits afforded by coupling VUV detection to multi-dimensional GC chromatography (described below) could also be employed in these higher dimensional implementations.

In one application of GC×GC, a primary column having a nonpolar stationary phase such as dimethyl polysiloxane is used to separate the constituents of a sample essentially by boiling point, while a secondary column having a significantly different phase further separates the constituents according to some other property of their chemistry. The secondary column is often a much shorter column having a phase of larger degree of polarity than the primary column. For example, the secondary column may retain aromatic compounds more strongly than saturated compounds, providing a further degree of separation than a simple boiling point separation. The secondary column may additionally or alternately retain isoparaffins and naphthenes differently, so that the primary column provides an essentially boiling-point separation and the secondary column provides further separation among saturated compounds.

Since the secondary column is often much shorter than the primary column, the extra degree of separation does not necessarily result in a substantially larger run time. When combined with the present disclosure, the use of GC×GC separation with VUV detection reduces the deconvolution burden of the VUV detector. This can be advantageous in situations where the VUV detector deals with certain types of coelutions better than others. In the case of fuel analysis, VUV spectra is very capable when deconvoluting aromatics, olefins, and saturated hydrocarbons. Deconvolution among the various saturated compounds is achieved, but the capability is not as robust as the deconvolution between aromatic, olefin, and saturated hydrocarbons. Therefore, removing the need to consider paraffins, isoparaffins, and naphthenes simultaneously may improve the overall robustness of a classification analysis. Coelution of saturated compounds with aromatics and olefins is still advantageously handled by deconvolution.

The benefits of coupling a VUV spectroscopic detector to a GC×GC separation are numerous. The dataset is inherently four-dimensional, providing a means of identification to elution events. When thorough GC×GC separations are done, various chemical classes of compounds are often eluted in particular time regions and segregated from other chemical compounds. VUV spectroscopic detection can be used to verify these class separations, since VUV spectra often show class-specific features.

As in standard one-dimensional chromatography, the most common GC×GC detector for organic compounds is the flame ionization detector. As is the case with standard GC-FID, the only means of identification is the elution time, which is now a two-dimensional coordinate. Any shift in the retention times on either time axis can easily lead to misidentification, causing errors in quantitation of the measured samples. This means that retention times in two dimensions have to be accurately known and strictly controlled when using GC×GC-FID.

A concept similar to retention indices can be used for GC×GC data, but now the retention index scheme is also two dimensional, so two indices have to be maintained for each compound, one corresponding to each column. The retention indices are further dependent on the stationary phase of both primary and secondary column. The retention index "window" is now a retention index box. As in the case of one-dimensional chromatography, the size of these windows are very small when using FID detection. Since the VUV spectroscopic detector has an identification capability, corresponding retention index windows can be made significantly larger in both dimensions, significantly reducing the possibility of misidentification even when shifts in elution time occur. It is in principle possible to use GC×GC-VUV experiments for both identification and quantitation without prior knowledge of retention times. However, it is significantly easier to implement retention time/retention index constraints to GC×GC-VUV data due to the reduced requirements for retention time accuracy, and use of such constraints does not unduly complicate GC×GC-VUV analysis.

An embodiment of the present disclosure couples VUV spectroscopic detection to GC×GC separation to provide class and molecular identification capabilities. Instead of a single 3-D time×time×response chromatogram as provided by GC×GC-FID, GC×GC-VUV provides any number of 3-D chromatograms, one for each integration filter used. The integration filters can be selected to preferentially respond to particular molecular classes to provide a means of visual separation. For example, in fuel analysis, a 170-200 nm integration filter responds well to mono-aromatics, moderately well to olefins, but very little to saturated compounds. Consequently, a 3-D chromatogram consisting of time× time×VUV$_{170-200}$ where VUV$_{170-200}$ is the 170-200 nm integration response of the VUV data, shows strong $3^{rd}$ axis response in regions where mono-aromatics occur and very weak response where saturated compounds occur. Other compound classes can be similarly singled out: A 200-220 nm VUV integration filter responds well to PAHs based on two fused aromatic rings, like naphthalene and methylnaphthalene.

In cases where a filter that responds only to a class of interest can be defined, the total response of the filter can be summed or integrated to quantify the total amount of the molecular class present in the injected sample. The sum or integration may be constrained to a particular time region of the chromatogram to determine a peak or region "volume".

A further embodiment of the present disclosure extends the detailed approach described herein to apply to a multi-dimensional separation process. The predefined analysis windows are now two-dimensional analysis boxes. A predefined model consisting of a linear combination of reference spectra (e.g., Eq. 3) is associated with each analysis box, where the reference spectra correspond to the analytes that elute within the box. The deconvolution of the spectral data within the analysis box proceeds in a manner analogous to the one-dimensional separation case. Each spectrum within the box is fit according to the analysis model predefined for the box, resulting in a new response for each of the eluting constituents, consisting of the optimized $f_i$. If a strict deconvolution of a response filter is desired, each of the reference spectra can be integrated using that filter, and the optimized $f_i$ multiplied by these integration factors are the contribution from each of the analytes to the response filter. Quantitation can be done using the peak height/maximum or the total volume of the analyte's response. Relative quantitation can be done by applying calibration factors to these quantities, or by using Eq. 4, except that in this case the areas are understood to contain the corresponding analytes' total response. In other words, the areas in Eq. 4 are replaced with volumes.

The second dimension does not have to be graphically rendered in order to analyze the spectral data. The data as it arrives from the detector consists of periodic sections of elution events as analytes elute from the secondary column. In other words, the data as it is collected at the detector is still a two-dimensional dataset in the case of GC×GC-FID, or a three-dimensional dataset in the case of GC×GC-VUV. For example, if the modulation period is 6 seconds, the recorded data consists of response versus time, where each 6 second section is associated elution of a group of analytes from the primary column, with the responses from the group of analytes reordered according to their elution from the second column (so ideally the secondary separation is faster than 6 seconds). Further rendering the data according to primary and secondary time is useful for visualizing the data, but is not strictly necessary for quantitative processing, as long as the identity or class of a compounds that gave rise to the response in a particular region is known. Accordingly, the GC×GC-VUV dataset can be treated as a three-dimensional dataset that is converted into multiple two-dimensional datasets by the deconvolution, and quantitative responses treated as heights and areas, just as in the 1-D GC case. The predefined analysis windows are identified by which primary slice the window occurs in, and then a second set of time windows corresponding to the division of the secondary elution. After the deconvolution step of the detailed approach, a relative mass analysis like Eq. 4 can be directly applied.

Another embodiment of the present disclosure couples a VUV spectroscopic detector with a GC×GC separation, and uses the classification approach to analyze the VUV data. One way to define the time slices in this method is to associate a primary time with the modulation cycle, and divide the secondary column time into substantially equal slices. For example, the secondary time may be divided into halves or thirds. The classification approach can then be implemented in the same way as previously described for one-dimensional separation. The time slices can be analyzed in any order, as long as all of the slices are eventually analyzed. Information about both primary and secondary elution order can be used to supplement the analysis.

As an example, in the case of gasoline analysis a nonpolar phase primary column may be coupled with a secondary column having a phase that preferentially retains cyclic saturated hydrocarbons more than branched saturated hydrocarbons (or vice versa). The usual retention index scheme is used along with a retention index window to select a subset of the VUV reference library to consider for the tiered search stage of the classification approach. For each modulation cycle, a retention index is calculated from the retention time just as in the one-dimensional separation, and a subset of the VUV reference library selected consisting of analytes that elute within a particular RI window of the calculated RI. The secondary time can be divided into any number of slices that is convenient. When analyzing slices near the front of the cycle (that elute earliest) naphthenes are excluded from tiered search analyte lists. Isoparaffins are excluded from tiered search lists when analyzing secondary slices toward the end of the cycle, closer to the beginning of the next cycle. All other compound classes are treated as they were with the one-dimensional separation examples and in particular, it does not matter where aromatic and olefinic compounds elute in the secondary separation. The result is a rough boiling point separation of the entire sample as in the case of DHA or the 30 m nonpolar phase example shown earlier, with a further separation of the saturated hydrocarbons according to whether they are cyclic or noncyclic. All other coelutions are still allowed to occur. Other types of secondary separation can also be considered. For example, an ionic liquid phase can be used to further separate mono-aromatics, poly-aromatics, and saturated hydrocarbons from each other after a primary boiling point separation.

Another embodiment, a GC×GC-VUV separation is used specifically to provide analyte-specific or class-based reference spectra, which are then available for later use in less thorough separations. A GC×GC separation is in general more thorough than a one-dimensional GC separation. Specific compounds that coelute under ordinary one-dimensional GC separations may be separated by GC×GC experiments. In such cases, the absorbance spectra collected during a GC×GC-VUV experiment serve as reference spectra for those compounds and are added to the VUV reference library. Those reference spectra are available for identification or deconvolution, and in particular can be used to deconvolute the coeluting signals in the original one-dimensional separation.

In the context of the classification analysis, class-based reference spectra do not need to be specifically identified and can also consist of linear combinations of analyte reference spectra, as long as the analytes involved belong to the same class. Therefore, as long as the GC×GC-VUV experiment separated a complex sample into distinct class-based regions, the reference spectra obtained from the various regions can be used in a GC-VUV or GC×GC-VUV classification analysis, even if specific analyte identities are not always known.

As a particular example, a complex fuel mixture can be separated using a long analytical column containing a nonpolar stationary phase. For example, the primary column may be a 100 m column with a dimethyl polysiloxane phase. In this case, the primary separation is a high-resolution separation of the sample constituents by boiling point. This primary separation retains the gross retention characteristics of one-dimensional nonpolar phase chromatography, and in particular, molecular constituents elute according to the same approximate retention order and by carbon number. Therefore, the reference spectra collected at each cycle can be associated with a nonpolar retention order or retention index and also the compounds carbon number. The secondary separation further isolates the classes of the various hydrocarbons. For a GC×GC-VUV separation, the retention index is calculated from the primary axis elution time. Reference spectra are collected from the absorbance data within the cycle and class-identified based on either the VUV spectral shapes, the retention time along the secondary axis, or a combination of both. The carbon number is determined from a combination of primary elution time and the analyte class. All of this information is stored in the VUV reference library.

Multiple GC×GC-VUV experiments can be performed for this purpose. For example, a primary column of the type described above can be used in conjunction with different secondary column phases to preferentially isolate different compounds classes beyond the basic boiling point separation achieved by the primary column. One secondary column may provide regions of isolated naphthenes, for example, while another secondary phase may isolate mono- and poly-aromatics. The reference spectra need only be determined once, so the experiments used to determine them can be of arbitrary complexity.

Once the class-based reference spectra are determined, subsequent GC-VUV experiment can be substantially simpler. For example, a GC-VUV experiment can be run instead of a GC×GC-VUV experiment. A shorter column, faster temperature ramp, and higher flow rate can be used. The reference spectra are used in combination with the classification approach described earlier to deconvolve the total signal into contributions from the individual classes. The analysis can be further refined to quantify in terms of carbon number or to quantify certain individual compounds.

One embodiment records the absorbance as a function of wavelength and time. While the examples provided in this disclosure have specified a measured wavelength region from 125-240 nm it is noted that additional wavelengths above or below this region could also be beneficially employed. Furthermore, while certain embodiments described herein employ absorbance measurements, it is also noted that alternate embodiments are conceivable where other properties of the eluting compounds are instead measured. In particular, the transmittance of eluting compounds can be determined, being simply related to the absorbance. Corresponding adjustments to the fit methodology are necessary. Absorbance/transmittance data can also be supplemented with other measured quantities, such as fluorescence or other scattered radiation.

It will be recognized that as disclosed herein there is provided a particularly advantageous technique for deconvoluting signals, there are other types of deconvolution known in the art, and it will be recognized that the techniques disclosed herein need not be restricted to the particular deconvolution technique described. For example, Multivariate Curve Resolution (MCR), often used in conjunction with Alternating Least Squares (MCR-ALS). For example as disclosed in "Multivariate Curve Resolution (MCR). Solving the mixture analysis problem." A. de Juan, J. Jaumot, and R. Tauler. Anal. Methods, 2014, 6, 4964. One advantage to this type of algorithm is that it can provide the individual spectral profiles (i.e., absorbance spectra) as well as concentration profiles of compounds that coelute. One could conceive of running through a coelution event with such an algorithm, and then identifying the compounds via basic library search of the individual absorbance spectra. However, the conditions that must be met in order for the spectral profiles to be accurate are very restrictive: there has to be substantial separation of the compounds and the spectral profiles will likely not be accurate if this condition is not met.

While the methods detailed in this specification are advantageously applied to liquid samples introduced to a GC, samples that are inherently gaseous can also be analyzed. This may entail simply injecting the gaseous sample into an injection system similar to that used by liquids, only using a gas-tight syringe of appropriate volume. In other cases, the split/splitless (or other) inlet used to introduce the sample to the chromatographic column can be replaced by an appropriate gas introduction system, such as a gas manifold and valve system. In such cases, cryogenic techniques are often used to condense the introduced sample on the column, or special column phases are used to condense introduced analytes via phase focusing techniques. In such cases, the quality of the chromatographic separations can be poor compared to typical liquid chromatography and the advantageous aspects of both detailed and classification approaches, especially the ability to handle coelution and partial spectral saturation, are particularly helpful.

It will be recognized that as used herein, the use of GC separations includes what some may refer to as "Fast GC," a technique to speed up GC separations because such fast techniques can in principle be applied to any GC experiment. Thus, while the specific examples presented herein make use of nitrogen or helium carrier gas and standard capillary columns, none of the features of the disclosed method preclude the use of hydrogen carrier gas, shorter capillary columns having narrower inner diameters, or other separation techniques often referred to in the art as "fast GC". The application of these separation conditions individually or in combination when practicing the present techniques has the potential for further speed improvements versus more traditional carrier gas and/or column choices. It will further be recognized that even for "normal" GC separations, temperature ramps and flow rates could be further optimized, all as would be recognized by one skilled in the art.

Though the analysis techniques described herein are presented in conjunction with a gas chromatograph which elutes gas analytes, it will be recognized that the techniques described herein may be utilized in conjunction with other chromatography systems. Thus, for example, the techniques may be utilized with liquid chromatography systems which elute liquid analytes. Such techniques may include both traditional liquid chromatography and high performance liquid chromatography (also referred to as high pressure liquid chromatography). Other chromatography systems may also be utilized.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as presently preferred embodiments. Equivalent elements and techniques may be substituted for those illustrated and describe herein and certain features of the invention may be utilized independently of the use of other features, all as would be apparent to one skilled in the art after having the benefit of this description of the invention.

What is claimed is:

1. A method of analyzing a multi-constituent chemical sample, comprising:
   providing a chromatograph, the chromatograph configured to elute from the chemical sample a plurality of analytes to be analyzed;
   providing a spectrometer to analyze the plurality of analytes, the spectrometer capable of measuring multiple wavelengths of light, and when coupled with the chromatograph providing wavelength dependent and time dependent chromatographic data;
   dividing the chromatographic data into a plurality of time segments;
   generating a total chromatographic response for each time segment;
   determining contributions of one or more of the analytes that elute in a particular time segment, the determining contributions accomplished, at least in part, by applying, for at least some of said time segments, a deconvolution model to the total chromatographic response; and
   combining, for one or more time segments, results from applying the deconvolution model to determine the contribution of individual or groups of analytes of the multi-constituent chemical sample,
   wherein the deconvolution model comprises a combination of reference responses for each of the analytes analyzed.

2. The method of claim 1, wherein the determining step comprises:
   using the total chromatographic response and the deconvolution model in combination with a tiered search to predict the identities of analytes eluting during the particular time segment, wherein the deconvolution model comprises a combination of reference responses for analytes considered in the tiered search,
   wherein use of the deconvolution model results in a determination of contributions of each of the reference responses to the total chromatographic response for the particular time segment.

3. The method of claim 2, wherein the chromatograph is a gas chromatograph.

4. The method of claim 3, wherein the tiered search is restricted to analytes having retention indices within a specified range.

5. The method of claim 3, wherein at least one of the analytes predicted by the tiered search is of same class as the actual analyte in the sample, but is not an exact match to the actual analyte in the sample.

6. The method of claim 3, wherein contributions of analytes of a same chemical class are summed and reported as a single class contribution.

7. The method of claim 3, wherein contributions of analytes of a same carbon number are summed and reported as a single carbon number contribution.

8. The method of claim 3, wherein for each time segment the total chromatographic response is generated by summing chromatographic data for each time point in the time segment.

9. The method of claim 2, wherein the tiered search is a fit of a total absorbance spectrum to a list of reference analyte spectrums, the fit first being performed for single analyte reference spectrums within the list and then the fit next being performed for reference analyte spectrums for two or more analytes.

10. The method of claim 1, wherein the time segments are of equal length.

11. The method of claim 1, wherein the time segments are selected automatically using a peak integration routine.

12. The method of claim 1, wherein the time segments and/or chromatographic separation conditions are selected such that three or fewer analytes elute during each time segment.

13. The method of claim 1, wherein the deconvolution model includes a background response component.

14. The method of claim 1, wherein the deconvolution model is determined via application of a tiered library search.

15. The method of claim 1, wherein a fit metric is used to verify the results of the deconvolution model.

16. The method of claim 1, wherein the contribution of individual analytes of the multi-constituent chemical sample is used to yield at least one of an elution time, a peak height, a peak sum or a peak area.

17. The method of claim 1, wherein relative concentrations of the plurality of analytes are determined.

18. The method of claim 1, wherein concentrations or amounts of at least one of the plurality of analytes are determined by utilizing peak height and/or a peak area.

19. The method of claim 1, wherein the chromatograph is a gas chromatograph.

20. The method of claim 1, wherein the wavelength dependent and time dependent chromatographic data is absorbance data.

21. A chemical analysis system comprising:
a gas chromatograph, the gas chromatograph configured to eluate from a chemical sample a plurality of analytes to be analyzed;
a spectrometer to analyze the plurality of analytes, the spectrometer capable of measuring multiple wavelengths of light; and
a computer coupled to the spectrometer, data from spectrometer provided to the computer, the computer configured to:
represent data from the spectrometer as wavelength dependent and time dependent chromatographic data, the chromatographic data divided into a plurality of time segments;
generating a total chromatographic response for the particular time segment;
determine contributions of one or more of the analytes that elute in a particular time segment, the determining contributions accomplished, at least in part, by applying, for at least some of said time segments, a deconvolution model to the total chromatographic response; and
combine, for one or more time segments, results from applying the deconvolution model to determine the contribution of individual or groups of analytes of the chemical sample,
wherein the deconvolution model comprises a combination of reference responses for each of the analytes analyzed.

22. The system of claim 21, wherein the computer determines contributions of one or more of the analytes that elute in a particular time segment by a technique that comprises:
using the total chromatographic response and the deconvolution model in combination with a tiered search to predict the identities of analytes eluting during the particular time segment, wherein the deconvolution model comprises a combination of reference responses for analytes considered in the tiered search,
wherein use of the deconvolution model results in a determination of contributions of each of the reference responses to the total chromatographic response for the particular time segment.

23. The system of claim 21, wherein the spectrometer provides analysis for wavelengths of light that includes at least vacuum ultraviolet light wavelengths.

24. The system of claim 23, wherein the spectrometer has a two-dimensional detector capable of measuring multiple wavelengths of light simultaneously.

25. The method of claim 22, wherein the tiered search is a fit of a total absorbance spectrum to a list of reference analyte spectrums, the fit first being performed for single analyte reference spectrums within the list and then the fit next being performed for reference analyte spectrums for two or more analytes.

26. A method of analyzing a multi-constituent chemical sample, comprising:
providing a gas chromatograph, the gas chromatograph configured to eluate from the chemical sample a plurality of analytes to be analyzed;
providing a spectrometer having a two-dimensional detector to analyze the plurality of analytes;
representing data from the spectrometer analysis as wavelength dependent and time dependent chromatographic data, the chromatographic data divided into a plurality of time segments;
for each time segment:
summing chromatographic data for multiple time points in the time segment;
generating a total chromatographic response for the time segment using the summed chromatographic data;
using the total chromatographic response and a deconvolution model in combination with a tiered search to automatically predict identities of analytes eluting during the time segment; and
determining a contribution of each of the referenced responses to the total chromatographic response for the time segment through using deconvolution model; and
combining results from the determining step of each time segment to provide a total contribution of each analyte predicted to be present in the multi-constituent chemical sample.

27. The method of claim 26, wherein the wavelength dependent and time dependent chromatographic data is absorbance data.

28. The method of claim 27, wherein the spectrometer provides analysis for wavelengths of light that includes at least vacuum ultraviolet light wavelengths.

29. The method of claim 27, wherein the tiered search is restricted to analytes having retention indices within a specified range.

* * * * *